(12) United States Patent
Tupin, Jr. et al.

(10) Patent No.: US 9,078,582 B2
(45) Date of Patent: Jul. 14, 2015

(54) FETAL MONITORING DEVICE AND METHODS

(75) Inventors: Joe Paul Tupin, Jr., Truckee, CA (US);
Joe Paul Tupin, El Macero, CA (US);
Stephan Stephansen, IV, Los Altos, CA (US)

(73) Assignee: LifeWave Biomedical, Inc., Los Altos, CA (US)

( * ) Notice: Subject to any disclaimer, the term of this patent is extended or adjusted under 35 U.S.C. 154(b) by 0 days.

(21) Appl. No.: 13/246,784

(22) Filed: Sep. 27, 2011

(65) Prior Publication Data
US 2012/0041281 A1 Feb. 16, 2012

Related U.S. Application Data

(63) Continuation of application No. 12/765,680, filed on Apr. 22, 2010, now abandoned.

(60) Provisional application No. 61/171,772, filed on Apr. 22, 2009.

(51) Int. Cl.
*A61B 5/05* (2006.01)
*A61B 5/0444* (2006.01)
(Continued)

(52) U.S. Cl.
CPC ............... *A61B 5/0444* (2013.01); *A61B 5/05* (2013.01); *A61B 5/4362* (2013.01);
(Continued)

(58) Field of Classification Search
CPC .. A61B 5/4362; A61B 5/0444; A61B 5/6823; A61B 5/1113; A61B 5/1114; A61B 5/024; A61B 5/7271

USPC ............ 600/407, 481, 301; 128/920
See application file for complete search history.

(56) References Cited

U.S. PATENT DOCUMENTS

| 4,373,527 A | 2/1983 | Fischell |
| 4,848,354 A | 7/1989 | Angelsen et al. |

(Continued)

FOREIGN PATENT DOCUMENTS

| DE | 10345717 A1 | 4/2005 |
| JP | 2001-522707 A | 11/2001 |

(Continued)

OTHER PUBLICATIONS

McKee et al.; The natural history of congestive heart failure: the Framingham study; N. Engl. J. Med.; vol. 285; No. 26; pp. 1441-1446; 1971.

(Continued)

*Primary Examiner* — Rochelle Turchen
(74) *Attorney, Agent, or Firm* — Shay Glenn LLP

(57) ABSTRACT

Described herein are fetal and/or maternal monitoring devices, systems and methods using UWB medical radar. These devices and systems may include a UWB sensor providing high-resolution and reliable simultaneous monitoring of multiple indicators of fetal and/or maternal health, such as fetal heart rate, fetal heart rate variability, fetal respiration, fetal gross body movement, maternal contractions, maternal heart rate, maternal respiration, and other derivative parameters during virtually all stages of pregnancy and during delivery. The sensor allows novel collection of physiological data using a single sensor or multiple sensors to develop individual and aggregate normal motion indices for use in determining when departure from normal motion index is indicative of fetal or maternal distress.

26 Claims, 10 Drawing Sheets

(51) Int. Cl.
  *A61B 5/00*   (2006.01)
  *G01S 13/02*  (2006.01)
  *G01S 13/56*  (2006.01)
  *G01S 13/88*  (2006.01)
  *A61B 8/00*   (2006.01)

(52) U.S. Cl.
  CPC ............. *A61B 5/6823* (2013.01); *A61B 8/565* (2013.01); *G01S 13/0209* (2013.01); *G01S 13/56* (2013.01); *G01S 13/88* (2013.01)

(56) References Cited

U.S. PATENT DOCUMENTS

| | | | |
|---|---|---|---|
| 4,901,725 A | | 2/1990 | Nappholz et al. |
| 4,984,576 A | | 1/1991 | Schulenberg et al. |
| 5,036,248 A | | 7/1991 | McEwan et al. |
| 5,088,498 A | * | 2/1992 | Beach et al. .................. 600/453 |
| 5,097,837 A | * | 3/1992 | Reuschel ...................... 600/453 |
| 5,257,627 A | * | 11/1993 | Rapoport ...................... 600/437 |
| 5,271,055 A | | 12/1993 | Hsieh et al. |
| 5,274,271 A | | 12/1993 | McEwan |
| 5,292,348 A | | 3/1994 | Saumarez et al. |
| 5,345,471 A | | 9/1994 | McEwan |
| 5,361,070 A | | 11/1994 | McEwan |
| 5,457,394 A | | 10/1995 | McEwan |
| 5,465,094 A | | 11/1995 | McEwan |
| 5,510,800 A | | 4/1996 | McEwan |
| 5,511,553 A | | 4/1996 | Segalowitz |
| 5,512,834 A | | 4/1996 | McEwan |
| 5,517,198 A | | 5/1996 | McEwan |
| 5,519,400 A | | 5/1996 | McEwan |
| 5,521,600 A | | 5/1996 | McEwan |
| 5,523,760 A | | 6/1996 | McEwan |
| 5,540,733 A | | 7/1996 | Testerman et al. |
| 5,560,363 A | | 10/1996 | Torp et al. |
| 5,563,605 A | | 10/1996 | McEwan |
| 5,573,012 A | | 11/1996 | McEwan |
| 5,576,627 A | | 11/1996 | McEwan |
| 5,581,256 A | | 12/1996 | McEwan |
| 5,589,838 A | | 12/1996 | McEwan |
| 5,609,059 A | | 3/1997 | McEwan |
| 5,610,611 A | | 3/1997 | McEwan |
| 5,630,216 A | | 5/1997 | McEwan |
| 5,661,385 A | | 8/1997 | McEwan |
| 5,662,115 A | | 9/1997 | Torp et al. |
| 5,682,164 A | | 10/1997 | McEwan |
| 5,736,958 A | | 4/1998 | Turpin |
| 5,738,102 A | | 4/1998 | Lemelson |
| 5,754,144 A | | 5/1998 | McEwan |
| 5,757,320 A | | 5/1998 | McEwan |
| 5,758,652 A | | 6/1998 | Nikolic |
| 5,766,208 A | | 6/1998 | McEwan |
| 5,767,953 A | | 6/1998 | McEwan |
| 5,774,091 A | | 6/1998 | McEwan |
| 5,805,110 A | | 9/1998 | McEwan |
| 5,820,561 A | | 10/1998 | Olstad et al. |
| 5,832,772 A | | 11/1998 | McEwan |
| 5,853,005 A | | 12/1998 | Scanlon |
| 5,883,591 A | | 3/1999 | McEwan |
| 5,980,463 A | | 11/1999 | Brockway et al. |
| 6,031,421 A | | 2/2000 | McEwan |
| 6,126,611 A | | 10/2000 | Bourgeois et al. |
| 6,185,457 B1 | | 2/2001 | Kroll et al. |
| 6,213,947 B1 | | 4/2001 | Phillips |
| 6,233,479 B1 | | 5/2001 | Haddad et al. |
| 6,292,433 B1 | | 9/2001 | Gilbert et al. |
| 6,325,761 B1 | | 12/2001 | Jay |
| 6,348,898 B1 | | 2/2002 | Rosenbury et al. |
| 6,373,428 B1 | | 4/2002 | McEwan |
| 6,414,627 B1 | | 7/2002 | McEwan |
| 6,454,711 B1 | | 9/2002 | Haddad et al. |
| 6,454,719 B1 | | 9/2002 | Greenhut |
| 6,471,689 B1 | | 10/2002 | Joseph et al. |
| 6,491,639 B1 | | 12/2002 | Turcott |
| 6,535,161 B1 | | 3/2003 | McEwan |
| 6,676,608 B1 | 1/2004 | Keren |
| 6,738,044 B2 | 5/2004 | Holzrichter et al. |
| 6,753,783 B2 | 6/2004 | Friedman et al. |
| 6,829,378 B2 | 12/2004 | DiFilippo et al. |
| 6,899,684 B2 | 5/2005 | Mault et al. |
| 6,914,552 B1 | 7/2005 | McEwan |
| 6,944,107 B2 | 9/2005 | Fukushima et al. |
| 6,984,207 B1 | 1/2006 | Sullivan et al. |
| 7,003,348 B1 | 2/2006 | Brewer et al. |
| 7,025,729 B2 | 4/2006 | de Chazal et al. |
| 7,075,485 B2 | 7/2006 | Song et al. |
| 7,224,944 B2 | 5/2007 | McEwan |
| 7,226,427 B2 | 6/2007 | Steen |
| 7,294,105 B1 | 11/2007 | Islam |
| 7,304,580 B2 | 12/2007 | Sullivan et al. |
| 7,305,052 B2 | 12/2007 | Spiridon et al. |
| 7,432,847 B2 | 10/2008 | Fedotov et al. |
| 7,652,581 B2 | 1/2010 | Gentry et al. |
| 7,654,962 B2 | 2/2010 | Sullivan |
| 7,725,150 B2 | 5/2010 | Tupin, Jr. et al. |
| 7,970,475 B2 | 6/2011 | Tehrani et al. |
| 2002/0032383 A1 | 3/2002 | Weil et al. |
| 2002/0156379 A1 | 10/2002 | Angelsen et al. |
| 2003/0088180 A1 | 5/2003 | Van Veen et al. |
| 2003/0090407 A1 | 5/2003 | Santhoff |
| 2004/0049118 A1 | 3/2004 | Ideker et al. |
| 2004/0100376 A1 | 5/2004 | Lye et al. |
| 2004/0111045 A1 | 6/2004 | Sullivan et al. |
| 2004/0123667 A1 | 7/2004 | McGrath |
| 2004/0249257 A1 | 12/2004 | Tupin, Jr. et al. |
| 2005/0052322 A1 | 3/2005 | Park et al. |
| 2005/0085687 A1 | 4/2005 | Mackin et al. |
| 2005/0101841 A9 | 5/2005 | Kaylor et al. |
| 2005/0267376 A1 | 12/2005 | Marossero et al. |
| 2006/0058681 A1 | 3/2006 | Eberle et al. |
| 2006/0094937 A1 | 5/2006 | Immoreev et al. |
| 2006/0154642 A1 | 7/2006 | Scannell, Jr. |
| 2006/0200033 A1 | 9/2006 | Keren et al. |
| 2006/0241409 A1 | 10/2006 | Winters et al. |
| 2006/0274031 A1 | 12/2006 | Yuen et al. |
| 2007/0027367 A1 | 2/2007 | Oliver et al. |
| 2007/0043585 A1 | 2/2007 | Matos |
| 2007/0055164 A1 | 3/2007 | Huang et al. |
| 2007/0135866 A1 | 6/2007 | Baker et al. |
| 2007/0156031 A1 | 7/2007 | Sullivan et al. |
| 2007/0161883 A1 | 7/2007 | Ayari et al. |
| 2007/0276270 A1 | 11/2007 | Tran |
| 2008/0001735 A1 | 1/2008 | Tran |
| 2008/0004904 A1 | 1/2008 | Tran |
| 2008/0009685 A1 | 1/2008 | Kim et al. |
| 2008/0027337 A1 | 1/2008 | Dugan et al. |
| 2008/0058740 A1 | 3/2008 | Sullivan et al. |
| 2008/0119896 A1 | 5/2008 | Wong et al. |
| 2008/0129511 A1 | 6/2008 | Yuen et al. |
| 2008/0146938 A1 | 6/2008 | Hazard et al. |
| 2008/0169931 A1 | 7/2008 | Gentry et al. |
| 2008/0243431 A1 | 10/2008 | Wai |
| 2008/0294019 A1 | 11/2008 | Tran |
| 2009/0022379 A1 | 1/2009 | Tashiro et al. |
| 2009/0048500 A1 | 2/2009 | Corn |
| 2009/0054737 A1 | 2/2009 | Magar et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076401 A1 | 3/2009 | Mazar et al. |
| 2009/0076405 A1 | 3/2009 | Amurthur et al. |
| 2009/0076410 A1 | 3/2009 | Libbus et al. |

(56) References Cited

U.S. PATENT DOCUMENTS

| | | |
|---|---|---|
| 2009/0076559 A1 | 3/2009 | Libbus et al. |
| 2009/0203972 A1 | 8/2009 | Heneghan et al. |
| 2009/0227882 A1 | 9/2009 | Foo |
| 2009/0238426 A1 | 9/2009 | Fear et al. |
| 2010/0179421 A1 | 7/2010 | Tupin, Jr. |
| 2010/0234720 A1 | 9/2010 | Tupin, Jr. et al. |
| 2010/0274145 A1 | 10/2010 | Tupin, Jr. et al. |
| 2011/0060215 A1 | 3/2011 | Tupin, Jr. et al. |
| 2011/0112403 A1 | 5/2011 | Machtey et al. |
| 2011/0172540 A1 | 7/2011 | Jackson |
| 2011/0282228 A1 | 11/2011 | Shiner et al. |
| 2013/0245436 A1 | 9/2013 | Tupin, Jr. et al. |

FOREIGN PATENT DOCUMENTS

| | | |
|---|---|---|
| JP | 2002-538872 A | 11/2002 |
| WO | WO01/70103 A2 | 9/2001 |
| WO | WO2007/027660 A2 | 3/2007 |
| WO | WO2007/101343 A1 | 9/2007 |
| WO | WO2007/120904 A2 | 10/2007 |
| WO | WO2007/124126 A2 | 11/2007 |
| WO | WO2007/143535 A2 | 12/2007 |
| WO | WO2008/057883 A2 | 5/2008 |
| WO | WO2009/029453 A2 | 3/2009 |
| WO | WO2009/036256 A1 | 3/2009 |
| WO | WO2009/036306 A1 | 3/2009 |
| WO | WO2009/036313 A1 | 3/2009 |

OTHER PUBLICATIONS

Neubauer, Stefan; The failing heart—an engine out of fuel; N. Engl. J. Med.; vol. 356; No. 11; pp. 1140-1151; 2007.

Tupin, Jr. et al.; A novel ultra-wideband sensor used for cardiopulmonary monitoring; 5 pgs.; Mar. 9, 2009.

Tupin, Jr. Joe P.; U.S. Appl. No. 13/196,139 entitled "Ultra wideband (UWB) baby monitors for detection of infant cardiopulmonary distress," filed Aug. 2, 2011.

Luo et al.; A two-layer dielectric absorber covering a wide frequency range; Ceramics Int; 33(2):197-200; Mar. 2007.

Staderini, Enrico M.; UWB Radars in Medicine; IEEE Aerospace and Electronic Systems; 17(1):13-18; Jan. 2002.

Tupin, Jr.; U.S. Appl. No. 13/902,623 entitled "System and Method for Non-Invasive Instantaneous and Continuous Measurement of Cardiac Chamber Volume," filed May 24, 2013.

Wells; Biomedical Ultrasonics; Academic Press; pp. 54; Mar. 1977.

Dissanayake et al.; UWB antenna impedance matching in biomedical implants, antennas and propagation; EuCAP; pp. 3523-3526; 2009 (year of pub. sufficiently earlier than effective US filing date and any foreign priority date).

Li et al.; The parameters selection of matching layer of ultrasonic transducers; Journal of Shaanxi Normal University (Natural Science Edition); 37(5); pp. 38-41; Sep. 30, 2009 (Chinese w/ English Abs. and CN Office Action).

Zhao; The application of acoustic matching of air-media ultrasonic converter; Automated Instrumentation; 16(12); pp. 18-21; Dec. 31, 1995 (Chinese w/ English Abs. and CN Office Action).

\* cited by examiner

FETAL MONITORING DEVICE AND METHODS

CROSS REFERENCE TO RELATED APPLICATIONS

This patent application is a continuation of U.S. patent application Ser. No. 12/765,680, filed Apr. 22, 2010, which claims priority to U.S. Provisional Patent application Ser. No. 61/171,772, filed on Apr. 22, 2009.

This application may be related to U.S. patent application Ser. No. 12/759,909, filed on Apr. 14, 2010, and titled "SYSTEM AND METHOD FOR EXTRACTING PHYSIOLOGICAL DATA USING ULTRA-WIDEBAND RADAR AND IMPROVED SIGNAL PROCESSING TECHNIQUES."

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

The devices and method described herein relate to the field of fetal monitors for physiological monitoring of mother and fetus. In particular, the present invention relates to sensors using ultra-wideband (UWB) medical radar and analytical techniques and software for non-invasively monitoring and tracking one or more indicators of fetal and/or maternal health.

BACKGROUND OF THE INVENTION

Ultra-wideband (UWB) is a relatively new term to describe a technology that had been known since the early 1960's as "carrier-free", "baseband" or "impulse" technology. The transmitted spectrum from a UWB device differs from those of radio, television and radar systems which emit a narrow band signal with bandwidths typically less than 10% of the central frequency, while a UWB spectrum may have a bandwidth of 50% or more of the central frequency. Because of this extremely wide bandwidth, UWB devices have advantages over more traditional systems. They can carry or collect significantly larger amounts of data, operate at much lower power levels, are less susceptible to multi-path interference, and can better penetrate a variety of materials.

The basic concept behind UWB is to generate, transmit, and receive an extremely short duration burst of radio frequency (RF) energy—typically a few tens of picoseconds (trillionths of a second) to a few nanoseconds (billionths of a second) in duration. These bursts consist of one to only a few cycles of an RF carrier wave. The resultant waveforms are extremely broadband, so much so that it is often difficult to determine an actual RF center frequency—thus, the term "carrier-free". The short pulse duration also allows the radar to 'see' at much closer distances and at finer resolutions than more traditional systems.

With its ultra low power pulses, and fine resolution imaging capabilities, the technology can be used for many biomedical applications, such as the fetal monitoring system we are presenting. Statistics have shown that there is a great need for fetal monitoring outside of the hospital environment for at risk pregnancies. There are over 6 million pregnancies resulting in 4.2 million registered births in the United States each year. Of these pregnancies, approximately 10% are classified as high-risk where high-risk denotes an increased incidence of maternal or fetal illness or death or an increased complication rate either before or after delivery. There are a number of conditions or characteristics—known as risk factors, which make a pregnancy high risk. Some of these risk factors are present in the mother-to-be prior to pregnancy, with examples including young or old maternal age, being overweight or underweight, having had problems in previous pregnancies, or pre-existing health conditions, such as high blood pressure, diabetes, or HIV. Other risk factors can develop during pregnancy, including preeclampsia and eclampsia, gestational diabetes mellitus, bacterial vaginosis, bleeding, cholestasis of pregnancy, incompetent cervix, and placenta accrete. Doctors identify and attempt to quantify these factors to determine the degree of risk for a particular woman and baby, allowing the physician to tailor pre- and post-natal care to minimize risk.

There are a variety of procedures available to help quantify the risks and track fetal development. One particular test, the Non-Stress Test (NST), is commonly used to evaluate the fetus' heart rate variability over a finite period of time at regular intervals during pregnancy. A fetal monitor is typically used to measure the fetus' heart rate in response to its movements.

Ultrasonic and electronic fetal heart rate monitoring are commonly used to assess fetal well-being prior to and during labor. Although fetal monitoring allows the detection of fetal compromise or distress, there are also risks associated with currently available and implemented methods of fetal monitoring, including false-positives that may result in unnecessary surgical intervention. Since variable and inconsistent interpretation of fetal heart rate tracings may affect management of a pregnancy, a systematic approach to interpreting the patterns is important.

Fetal heart rate undergoes constant and minute adjustments in response to the fetal environment and stimuli. Fetal heart rate patterns are classified as reassuring, non-reassuring or ominous. Non-reassuring patterns such as fetal tachycardia, bradycardia and late decelerations with good short-term variability typically require intervention to rule out fetal acidosis. Ominous patterns require emergency intrauterine fetal resuscitation and immediate delivery. Differentiating between a reassuring and non-reassuring fetal heart rate pattern is the essence of accurate interpretation, which is essential to guide appropriate triage decisions.

Auscultation of the fetal heart rate (FHR) is performed by external or internal means. External monitoring is performed using a hand-held Doppler ultrasound probe to auscultate and count the FHR during a uterine contraction and for 30 seconds thereafter to identify fetal response. It may also be performed using an external transducer, which is placed on the maternal abdomen and held in place by an elastic belt or girdle. The transducer uses Doppler ultrasound to detect fetal heart motion and is connected to an FHR monitor. The monitor calculates and records the FHR on a continuous strip of paper. Recently, second-generation fetal monitors have incorporated microprocessors and mathematic procedures to improve the FHR signal and the accuracy of the recording. However, it is well-known that existing ultrasonic measurement devices have frequent data dropouts and can cause erroneous measurements to be communicated as accurate assessments of FHR. For example, current ultrasonic FHR systems are known to insert false data suggesting elevated heart rate when, in actuality, the ultrasonic device is simply not picking up any signals for FHR. False data presentation can be caused by shifting of the fetus, the mother or of the sensor by the operator, causing the ultrasonic sensor to lose the signal, effectively creating a non-empirical assessment of FHR which tends to be double the actual FHR. This issue may be exacerbated by the need to ensure that the ultrasound FHR sensor is positioned properly to track the front of the Doppler pressure wave from the fetal heart beat. If the sensor is not properly positioned, it will not collect accurate data.

Internal monitoring is performed by attaching a screw-type electrode to the fetal scalp with a connection to an FHR monitor. The fetal membranes must be ruptured, and the cervix must be at least partially dilated before the electrode may be placed on the fetal scalp. The most important risk of electronic fetal heart rate monitoring is its tendency to produce false-positive results. Electronic fetal heart rate monitoring is associated with increased rates of surgical intervention resulting in increased costs and increased risk of complications to the mother and fetus. Studies show that 38 extra cesarean deliveries and 30 extra forceps operations are performed per 1,000 births with continuous electronic fetal heart rate monitoring versus intermittent auscultation. Variable and inconsistent interpretation of the fetal heart rate tracings by clinicians may affect management of patients. The effect of continuous electronic fetal heart rate monitoring on malpractice liability has not been well established.

Other rare risks associated with EFM include fetal scalp infection and uterine perforation with the intrauterine tocodynamometer or catheter. In light of certain limitations of existing technology, it would be extremely beneficial to provide a sensor capable of noninvasively monitoring fetal heart rate and other fetal indicators which would increase the reliability of measurements, minimize the potential for false-positives of fetal distress, eliminate the possibility of other complications from the monitoring methodology, improve maternal health, provide continuous monitoring to reliably identify normal base-line or reassuring behavior from non-reassuring or ominous behavior, and finally, improve decision making via accurate interpretation to maximize the probability of appropriate triage decisions. In particular, it would be beneficial to provide a sensor less reliant on specific positioning in proximity to the fetus and the fetal heart to ensure accurate FHR readings.

Furthermore, there is also a need to provide monitors capable of determining one or more indicators of maternal health, in addition to fetal health. Current systems and devices typically require multiple devices operating independently to determine one or more indicators of material and fetal health. This process takes additional time, and adds to the complexity of the procedure.

Finally it would be highly beneficial to provide a system for monitoring fetal and/or maternal health via ultra wide band (UWB) that is capable of modulating the power and energy level of the signals applied. Modulation of the applied power level may allow the system to prevent exposing the fetus and mother to unnecessarily high energy levels, as well as regulating the energy needs of the system.

Described herein are methods, devices and systems that may address the needs mentioned above.

SUMMARY OF THE INVENTION

Described herein are fetal and/or maternal monitors using ultra-wideband (UWB) medical radar. The UWB devices and systems described herein may be used as part of a monitoring system that includes one or more sensors (UWB sensors), a processor for processing the UWB signals and/or additional sensor signals, and may also include a memory for storing the raw or processed signals (or extracted data), and a communications module for communicating the raw or processed signals to an external server and/or network. The system may also include software, firmware, or hardware configured to allow monitoring, reporting, or storage of the signals or data, and may also include a physician or medical services provider interface for presenting patient information and/or for providing alerts regarding maternal and/or fetal health.

The devices, systems, and methods described herein are configured to allow simultaneous and/or concurrent monitoring of multiple parameters or indicators of fetal and/or maternal health. For example, the same "scan" (e.g., a single UWB pulse or series of pulses) may be processed to provide multiple indicators of fetal and/or maternal health, such as fetal body movement, fetal heart rate, fetal respiration (pseudo-respiration), maternal uterine contraction rate, maternal heart rate, maternal respiration, maternal blood pressure, etc. The devices and methods herein describe the formation of a matrix that may be indexed by depth of penetration, providing information on the various rates or frequencies of movement; the processor may analyze this matrix to extract some or all of the indicators of maternal and/or fetal health.

In some variations, the system may also be configured to dynamically monitor the mother and/or fetus and control the power provided based on the strength of the signal received. Thus, the output UWB signal may be increased or decreased in power as needed, limiting the power applied to the fetus and/or mother.

The systems and devices described herein may include multiple sensors, including multiple UWB sensors and/or multiple types of sensors (UWB and ultrasound, UWB and pressure sensors, UWB and temperature sensors, etc.). In variations having multiple UWB sensors, the sensor may include a single antenna for both transmission and receiving of UWB signals, or it may include one or more transmission antenna and one or more receiving antenna. When multiple UWB sensors are used, the system may be configured to provide monostatic or multistatic (e.g., bistatic) monitoring. In monostatic mode, the antenna(s) performing transmission (TX) and receiving (RX) are identical or co-located (e.g., traditional radar) while in multistatic mode, the system may switch the pairs of antenna used for transmission (TX) and receiving (RX). Alternatively, a single transmission antenna may be used with multiple receiving antennas. For example, the TX/RX antenna(s) at the top of the abdomen could transmit the pulse while one or more receive antennas positioned in other locations around the body could receive the reflections from the transmitted pulses. Multistatic techniques may be used to improve the quality of the reflected signal if a major surface of the fetal heart is not close to perpendicular to the direction of propagation (e.g., best reflections). These multistatic configurations (e.g., having two or more receive antennas) may also be configured to support forward scatter techniques. In forward scatter, one TX/RX antenna or pair of antennas are positioned at one location (e.g., on the left side of the mother's abdomen) and a second TX/RX antenna or pair of antenna are positioned at another location (e.g., on the right side of her abdomen), so that the TX signal from the first location is received by the RX antenna in the second location, and visa versa. These techniques may better isolate and track fetal activity.

These fetal monitoring devices and systems may be used either in a clinical (e.g., hospital) setting, or in some variations in a home setting.

For example, described herein are ultra-wideband (UWB) fetal monitoring systems capable of concurrent monitoring of indicators of fetal and maternal health, the system comprising: a sensor configured for receiving and transmission of UWB signal data, the sensor comprising at least one antenna; and a signal processor configured to receive signal data from the sensor and to process the information into a matrix of reflected signals indexed by depth and time, and to extract from the matrix a plurality of indicators of fetal or fetal and maternal health.

The sensor also includes a separate receiving antenna and a transmission antenna, or it may include a combined antenna configured for both receiving and for transmission. In some variations, the system includes a plurality of sensors that are each configured for receiving and transmission of UWB data and comprising at least one antenna. As mentioned, the system may be configured for monostatic operation, wherein the transmission of the UWB signal from each sensor is received by the same sensor, or for multistatic operation, wherein the transmission of a UWB signal from one sensor is received by a different sensor.

The signal processor may be configured to determine one or more indicators of fetal health selected from the group consisting of: fetal heart rate, fetal heart rate variability, fetal respiration, fetal body movement. The signal processor may be configured to determine one or more indicators of maternal health selected from the group consisting of: maternal heart rate, maternal contraction rate and strength, maternal blood pressure, maternal respiration.

In general, the system may also include a transmitter connected to the antenna, the transmitter configured to generate a series of low voltage, short-duration broadband pulses for transmission as an emitted signal from the antenna as an ultra-wide band spectrum signal. A receiver may be connected to the antenna, the receiver configured to receive reflections of emitted signals received by the antenna and process them into data to be passed on to the signal processor. The receiver may be configured to amplify signals based on their depth so that signals reflected further from the sensor are amplified more than signals reflected closer to the sensor.

The signal processor may be configured to specifically determine fetal heart rate and maternal contraction rate.

In some variations, the system also includes a local memory for storing the data and/or signals (e.g., the matrix information). The system may also include a communication module for communicating to a monitoring system. The monitoring system may comprise a computer system configured to store and transmit data. For example, the monitoring system may comprise a networked server.

In some variations, the sensor may be configured as a single-use, disposable sensor configured to couple and uncouple from the signal processor. For example, the sensor(s) may be an adhesive sensor that is configured to be attached (via an adhesive) to the mother's body. In other example, the sensor is configured to be worn or attached to the mother's clothing. In some variations, the sensors are configured to be durable and re-used.

In some variations, the system includes one or more non-UWB sensor(s), such as temperature sensors, heart-rate (pulse) sensors (e.g., for determining maternal heart rate), accelerometer's (for determining fetal or maternal movement), etc. Data from the non-UWB sensors may be integrated with the UWB data, and may be sent to the processor.

Also described herein are ultra-wideband (UWB) fetal monitoring systems capable of concurrent monitoring of indicators of fetal and maternal health. These systems may include: a sensor configured for receiving and transmission of UWB data, the sensor comprising at least one antenna; a transmitter connected to the antenna, the transmitter configured to generate a series of low voltage, short-duration broadband pulses for transmission as an emitted signal from the antenna as an ultra-wide band spectrum signal; and a signal processor configured to receive data from the sensor and to process the information into a matrix of reflected signals indexed by depth and time, and to extract fetal heart rate and maternal contraction rate from the matrix.

Also described herein are ultra-wideband (UWB) fetal monitoring systems configured for adaptive energy monitoring of indicators of fetal health, the system comprising: a sensor configured for receiving and transmission of UWB signal data, the sensor comprising at least one antenna; and a signal processor configured to receive signal data from the sensor and to process the information into a matrix of reflected signals indexed by depth and time, and to determine the energy level of signals reflected by the fetus; and a transmitted energy level adapter configured to adjust the energy level of the UWB signal transmitted by the sensor based on the energy level of the signals reflected by the fetus.

Any of the systems described herein may also include one or more outputs for presenting information about the fetus and/or mother. For example, an output may include a video monitor, strip/chart printer and/or recorder, printer, audio output, or the like.

The transmitted energy level adapter may include a comparator configured to compare the energy level of signals reflected by the fetus to a predetermined target energy level, wherein the transmitted energy level adapter is configured to adjust the energy level of the UWB signal to keep the energy level of signals reflected by the fetus within the predetermined target energy level.

Also described herein are ultra-wideband (UWB) fetal monitoring systems for monitoring indicators of fetal and maternal health. These system may include: a sensor configured for receiving and transmission of UWB data, the sensor comprising at least one antenna, a power source and a transmitter configured to generate a series of low voltage, short-duration broadband pulses for transmission as an emitted signal from the antenna as an ultra-wide band spectrum signal; a charging cradle configured to charge the power source; and a communications device configured to receive information from the sensor and to pass the information on to a signal processor, wherein the signal processor is configured to process the information into a matrix of reflected signals indexed by depth and time, to extract from the matrix a plurality of indicators of fetal or fetal and maternal health.

The signal processor may be configured to determine fetal heart rate and maternal contraction rate from the matrix. The system may also include an output configured to display one or more of the plurality of indicators of fetal or maternal health.

Also described herein are methods of simultaneously monitoring two or more indicators of fetal and maternal health using an ultra-wideband (UWB) system. The method may include the steps of: transmitting a series of low voltage, short-duration broadband pulses as emitted signals in an ultra-wide band spectrum toward a fetus; receiving reflected signals from the series of low voltage, short-duration broadband pulses; processing the reflected signals into a matrix indexed by depth and time; and extracting a first indicator of fetal health and a second indicator of fetal health or a first indicator of maternal health from the matrix.

In some variations, the method also includes displaying the first indicator of fetal health and the second indicator of fetal health or first indicator of maternal health. The method may also include positioning a sensor on or near a pregnant patient, wherein the sensor comprises an antenna configured for receiving and transmission of UWB data, the sensor comprising at least one antenna.

The step of processing the reflected signals may include dividing reflected signals corresponding to a single broadband pulse into a plurality of bins reflecting the depth of penetration of the broadband pulse.

In some variations, the step of extracting may include determining maternal contraction rate from the matrix and determining fetal heart rate from the matrix.

In general, the extracting step may be performed by first determining one or more landmarks that help differentiate between fetal and maternal regions within the matrix. For example, the step of extracting may include determining maternal contraction rate at a first depth from the matrix and determining maternal contraction rate at a second depth from the matrix, and determining the first indicator of fetal health by analyzing the region between the first and second depths from the matrix.

The method may also include the step of amplifying the reflected signals based on their depth, so that reflected signals deeper away from the transmission antenna are amplified more than reflected signals closer to the transmission antenna.

Also described herein are methods of simultaneously monitoring fetal and maternal health using an ultra-wideband (UWB) system during labor and delivery, the method comprising: positioning a sensor on a pregnant woman for intra-partum monitoring, the sensor configured for receiving and transmission of UWB data, the sensor comprising at least one antenna; transmitting a series of low voltage, short-duration broadband pulses as emitted signals in an ultra-wide band spectrum; receiving reflected signals from the series of low voltage, short-duration broadband pulses; processing the reflected signals into a matrix indexed by depth and time; and extracting fetal heart rate and maternal contraction rate from the matrix.

The devices, systems and methods described herein may provide remote fetal monitoring appropriate for the collection of NST data both within and outside of the clinical environment.

In some variations, the fetal monitor system will include at least one (UWB) sensor, a charging cradle, a communications device (or devices), and a processing station (e.g., server). The system may follow instructions provided by a physician. For example, in some variations, the system may be used for home-care. In this variation, the mother (or other caregiver) may, at prescribed times, initiate a test sequence by removing the sensor from the charging cradle and placing the sensor on the abdomen. An integrated speaker could be included to provide an audible signal proportional to the fetal heart beat to assist the mother in placement. Once properly positioned, the sensor will record data that may include fetal heart rate, fetal motion related to gross body movement and pseudo-respiration, and uterine contractions. The sensor may also connect to a detachable push button that the mother could use to manually mark fetal motion (a "kick counter"). The sensor could automatically terminate the test after the physician-specified time period, e.g., 5 min, 10 min, 30 minutes, etc., providing both an audible and visual prompt to the mother that the test is finished. At the conclusion of the test, the mother will return the sensor to the charging cradle.

Once the sensor-containing unit is returned to the charging cradle, the mother may retrieve the communication device (e.g., a smart phone) and launch the data transfer applet. The applet on the smart phone may activate a wireless Bluetooth connection between the sensor and phone, connect to the server via the cellular network, and upload the data to the server. At the conclusion of the upload, the mother will have the opportunity to append a short voice or text message to the data record before closing the session with the server. Once the test data has been uploaded to the server, the server will alert the mother's healthcare provider. The healthcare provider can then access the server through any device able to access the internet through a standard browser. After logging on, the healthcare provider can examine the data and if desired, run software that will analyze the data, identifying periods of fetal motion, fetal cardiac acceleration and deceleration, and uterine contractions. The analytical software will also calculate a fetal score based on the data to indicate the status of the fetus. After completing the data examination, the healthcare provider can send a message to the mother indicating the wellness of the fetus or asking the mother to contact the provider for a follow-up. Finally, at any time, the healthcare provider can enter in a series of dates that will result in prompts being sent on those dates to the mother to remind her to perform the tests.

Also described herein are systems for processing ultra-wideband (UWB) fetal monitoring data. For example, a system for processing UWB fetal (and fetal/maternal) data may include: a sensor configured for receiving and transmission of UWB data, the sensor comprising at least one antenna, a power source and a transmitter configured to generate a series of low voltage, short-duration broadband pulses for transmission as an emitted signal from the antenna as an ultra-wide band spectrum signal; and a signal processor configured to process UWB reflection data received by sensor to form a matrix of reflected signals indexed by depth and time from which a one or more indicators of fetal or fetal and maternal health may be extracted; and a server configured to receive information from the signal processor and to pass extracted indicators of fetal or fetal and maternal health on to one or more remote reporting stations.

The signal processor may be configured to extract a plurality of indicators of fetal or fetal and maternal health from the matrix. Any of the indicators described above may be extracted. In some variations, the server is configured to extract a plurality of indicators of fetal or fetal and maternal health from the matrix. Thus, extraction from the matrix may be performed at the individual signal processor level, or it may be sent from the patient-side device to a centralized server for processing. Thus, in some variations, the signal processor primarily conditions the signal and prepares it for passing on to the processor. Alternatively, the signal processor may extract information from the reflected signals. Extracting information may allow more efficient and streamlined transmission to the server. The server may be computer server sufficient for executing logic for processing the extracted information or for processing the matrix information to extract one or more indicators of fetal and/or maternal health.

In some variations, the server is configured to pass the extracted indicators on to one or more mobile devices. For example, the system may provide one or more accounts for a patients doctors, caregivers, etc. to access the patient data. This data may be sent directly to a physician or caregiver, or it may be accessed from a remote location by the physician/caregiver. In some variations the system is configured to send alerts to a physician/caregiver or other based on the indicator of fetal/maternal health.

DETAILED DESCRIPTION OF THE INVENTION

Any of the fetal monitoring systems described herein may include one or more UWB sensors for emitting UWB signals and for receiving reflections of the UWB signals and a processor configured to process the reflected UWB signals. The processor may be configured to organize the reflected signals into a matrix indexed by time and by depth into the tissue, or by frequency and depth into the tissue. The processor may also be configured to extract movement information specific to two or more indication of fetal and/or maternal health.

For example, in some variations, the fetal medical radar sensors described herein include a sensor (or "sensor unit") with associated electronics and/or logic. The logic may include hardware, firmware, and/or software to perform the functions described herein. The sensor 20 may include a transmitting (Tx) antenna and a receiving (Rx) antenna, or a combined transmitting/receiving antenna. The sensor 20 may communicate in a bidirectional mode with a processor, which may be part of an electronics housing. The electronics housing may also include a transceiver Tx/Rx, a transmitter circuit and a receiver circuit for delivering an electromagnetic signal to the transmitting antenna and for receiving reflected signals from the receiving antenna. The processor may be a central processor unit (CPU). In some variations, the sensor is integral to the processor, or it may be connected to it wirelessly or via a physical connection (e.g., wire). The system may also include data storage, an input for receiving raw data from the transceiver, and, and a power supply for the sensor.

Received or recorded raw data may be processed using specific logic (e.g., algorithms embodied in software operating on the CPU) in the processor and may be used to determine the plurality of indicators of fetal/maternal health.

Figure 1:
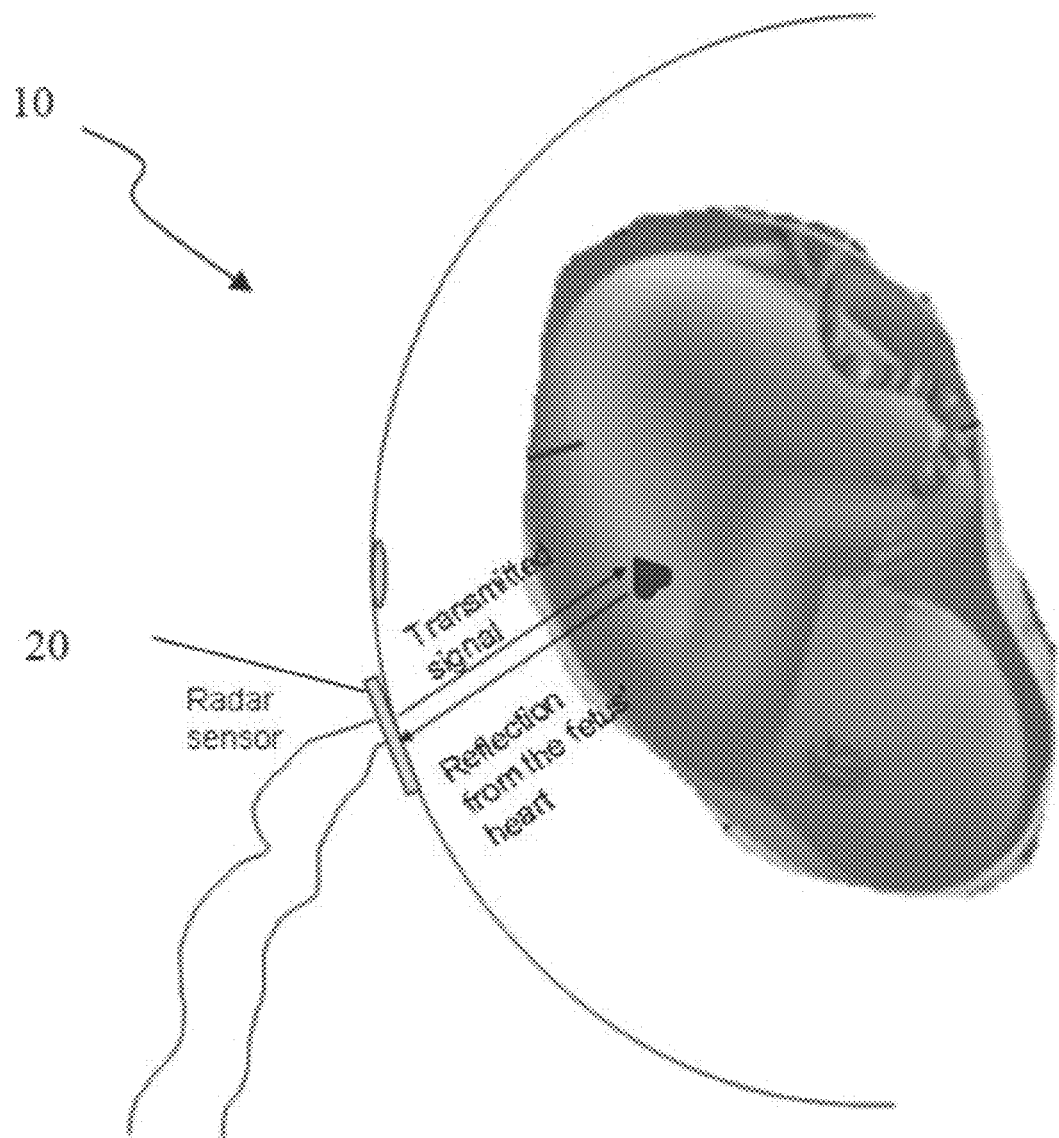
FIG. 1 is an illustration of one variation of a sensor coupled to a pregnant woman.

As illustrated in FIG. 1, in one example, the system may include a sensor 20, incorporating both transmitting and receiving antennas, that is placed on a pregnant woman's abdomen. The sensor 20 is connected in this example via a wire to a transceiver unit, which is placed to the side of the monitored subject. An audio cable from the transceiver unit is connected directly into a computer's audio input on the soundcard PCI. Logic embodied in (as software in this example) on the computer are then used to process and transform the raw data as described herein to determine, track and monitor the plurality of fetal and/or material health indicators.

In general, the systems described herein may monitor one or more indicator of fetal health (e.g., fetal heart rate, body movement, pseudo-respiration, etc.). In addition, the system may monitor simultaneously one or more indicator of maternal health (e.g., maternal heart rate, maternal respiration, maternal contraction rate/strength, etc.). In keeping with various regulatory requirements, including those standards required by both the United States Food and Drug Administration (FDA) and the United States Federal Communications Commission (FCC), the energy output of the sensor may be limited to a certain level to maximize subject safety. The current FDA limit for continuous public exposure to energy fields for all persons, including pregnant women, is 0.08 watts per kilogram (W/kg) for a whole body average and 1.6 W/kg for local exposure. The present invention includes a maximum average power output of only 0.8 mW, significantly less than the existing FDA limits by a factor of 1000. The fetus is exposed to even lower incident energy due to the attenuation of energy in the transmitted signal caused by absorption or reflection caused by the mother's skin, subcutaneous fat, uterine muscle, and amniotic fluid. As described herein, the system may also be further adapted to minimize the emitted energy by matching the emitted and reflected energy so that the system dynamically changes the emitted energy so that only a minimum level of energy is applied as necessary.

The electromagnetic energy, in the form of radio waves, transmitted by the sensor will produce a limited thermal effect on the subject, including the mother and the fetus. The average power output of the device is typically less than 0.001 mW/cm2. Again, maternal tissues absorb the predominant portion of this incident energy before it reaches the fetus. The fetal body temperature in the cardiac zone of interrogation would increase less than 0.001 degrees Celsius, well within acceptable ranges. To place this in context with other devices currently in widespread use, people are exposed daily to energy from microwave appliances, cell phones and wireless networks. The energy exposure of the systems described herein are typically over one thousand times less than the energy emitted from cell phones. Based on available evidence evaluating intrauterine effects of radio waves, and given the low energy output, the sensor is likely safe for use in humans with no known teratogenic effects which might disturb the growth or development of an embryo or fetus.

A transmit portion of the device or system typically produces a radio frequency signal that is sent through the sensor and transmitted toward the fetus. The timing of radio frequency signal release and transmission is synchronized to a corresponding receiver (e.g., Rx antenna) such that a receiving channel is never active before a transmit signal has been transmitted. The sensor 10 may be configured in any appropriate manner, including as a small rectangular strip having both a transmitting antenna and a receiving antenna. The strip may be configured to adhesively secure to the patients skin or clothing, or otherwise be attached to the patient. In some variations, the sensor elements are configured to be integral to a garment worn by the patient, or to the bed or bedding in which the patient is positioned.

The transmitting antenna typically delivers the transmitted signal toward the fetus while the receiving antenna picks up reflections of the transmitted signal. The receive antenna delivers the collected reflected signals back to the system, and may include a receiving pre-processor (or receiving circuitry) for processing the perceived signal prior to sending it to the processor. In some variations the pre-processor functions may be performed by the processor; alternatively, a separate device or circuit may be used. For example, a receiver circuit may receive raw reflected radar signals in packets driven by an interval of a receiver timing circuit which is continually synchronized with the transmitted signal. Within each signal packet, reflections of the transmitted signal at increasing depths are captured. Each packet of data may be amplified, for example, using a gain compensation circuit in which the front end of the packet is amplified the least and the back end of the packet is amplified the most. This may enhance reflections in deeper tissues which will attenuate more than reflections closer to the surface. Once the signal has been amplified, the signal may be passed through a series of low pass filters to prevent aliasing once the data becomes digitized.

In a one variation, the collected reflections and a timing synchronization (sync) signal are sent from the sensor to a processor; in parallel, the reflected and timing signals may be sent to an output, such as an audio or video output. For example, the reflected and timing signals may be sent through an audio cable connected to an audio output (e.g., a computer sound card). The two signals may be used to create a stereo signal for output, e.g., a left side of the stereo signal is the sync signal; a right side is the reflection signal. Logic may be used to output the signals (e.g., on a computer's sound card) while concurrently writing and saving the collected data for processing.

Figure 2A:
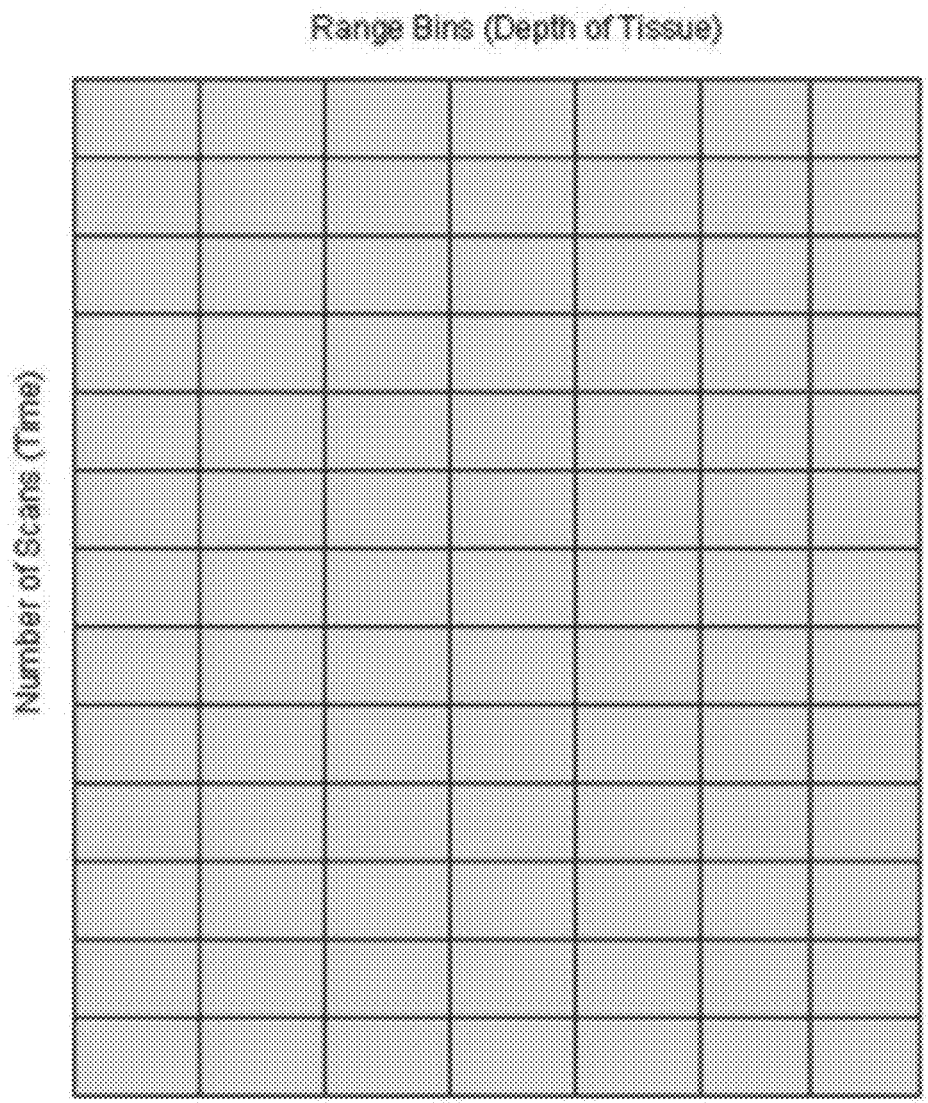
FIG. 2A is illustrates a time versus depth matrix as described herein.

Monitoring the plurality of indicators of fetal/maternal health may be performed by the processor, which may organize and analyze the data. For example, the processor may include logic for processing the data through a series of transformations to determine the plurality of indicators of fetal and/or maternal health. Collected and/or saved data (e.g., reflected data) may be reshaped into a matrix of the form illustrated in FIG. 2A, where streaming packets of data are aligned in columns. In this example, each data packet represents characteristics of the body (fetal and/or maternal) at various depths, also known as, range bins, at a particular sampling time. Analysis of the data within these range bins may be used to determine changes in dielectric characteristics of tissue based on the reflected signal, in the particular range bin to be correlated according to depth and time for further analysis.

The data from each range bin at a particular time representing a particular interrogation depth may be processed according to a filtering scheme. In another example, the data maybe representative of reflected intensity; alternatively the data maybe representative of frequency data. Filtering may be applied to the data within the matrix or as the data is entered into the matrix. One or more parameter may be determined based on the frequency composition of the signals within the matrix, and/or based on the relationship of the signals within one region of the matrix in comparison to other signals within the matrix. For example, fetal heart beat may be determined from other signals by ignoring signals that are outside a target frequency range. Other suppressed signals may be associated with other biological effects, electronic signals associated with the device, or other stray electronic signals in the ambient environment. For example, other signals may be determined based on the characteristic or expected frequency component, such as maternal respiration (~20 BPM), fetal respiration or pseudo-respiration (~50-60 BPM), and maternal heart rate (90-100 BPM). Fetal heart rate, in an expected range of 120-160 BPM, is the one target frequency range of interest. Thus, by scanning the matrix over time for frequencies within the expected ranges, predicted estimates may be determined. However, the expected ranges may be expanded to capture abnormal or out-of-range measurements, such as, for example, fetal heart rates which might indicate fetal distress.

In one example, the UWB sensor is programmed to sample the received signal resulting from transmitted energy being reflected from the mother's internal anatomical structures and the fetus. The sampler may be triggered by a variable time delay between the transmitter and the receiver sampler, where the time delay is equal to the time of flight from the transmit antenna to the anatomical depth of interest and finally to the receive antenna. This delay may be varied over a window in time corresponding to the anatomical region that includes the uterus and fetus and takes into account any additional delays required to compensate for circuit and propagation delays within the sensor.

Timing parameters for the UWB sensor may depend on the radar configuration, inherent circuit and propagation delays within the sensor, and the desired range of interrogation within the mother. For a UWB sensor configured for monostatic operation, for example, measured circuit and propagation delays within the sensor of 10 ns, and a desired anatomical range of 50 cm where 50 cm may be more than sufficient to cover the range from the mother's abdominal skin surface to her spine and thus, may ensure that the uterus and fetus are included. The minimum time delay may be set as 10 ns to account for the circuit and propagation delays within the sensor, while the maximum time delay may be set as 10 ns plus the round trip time of flight corresponding to 50 cm. Assuming an average dielectric constant of 50, the round trip time of flight is calculated to be approximately 24 ns, yielding a maximum time delay of 34 ns. The step size used to vary the sampler timing across the active 24 ns range window is set to 250 ps, providing a radial resolution of approximately 5 mm. Given the 24 ns range and 250 ps step size there will be 96 range bins in the range window.

The time delay may be swept across this range window at a rate that is significantly greater than the maximum frequency of interest to avoid aliasing in the digitized signal. Given a fetal heart rate expected range of 120-240 BPM or 2-4 Hz, the sweep rate may be set to 100 Hz. Each sweep if the range window produces a series of samples where the number of samples per discrete range bin is typically set to 4 or 8, allowing averaging for the samples at any single depth to reduce noise. Thus, with a 100 Hz sweep rate, 96 steps per sweep and 4 samples per step, the receiver sample rate will be approximately 38 k samples per second. Each set of 4 samples per range bin are averaged, yielding a effective sample rate of approximately 9.6 k samples per second.

Figure 2B:
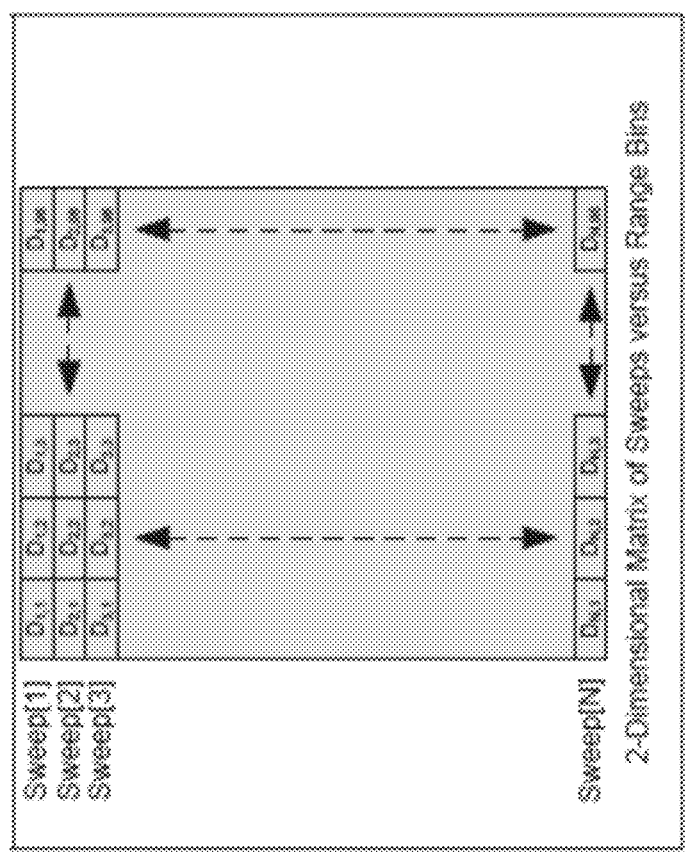
FIG. 2B is another variation of a matrix.

In some variations, such as the one illustrated in FIG. 2B, the time/range matrix may have a total of 96 columns where each column contains the averaged data for the corresponding range bin. The number of rows may depend on the type of physiological data desired and the algorithm needed to extract that data. Typically, the row count is set to allow storage of 1 to 5 minutes worth of data and is constantly updated with new data, providing a sliding window of data. Algorithms vary from simple differentiation and peak detection for identifying uterine contractions to more sophisticated motion detection algorithms where a moving average filter attenuates static returns and Fourier analysis techniques allow measurement of the fetal heart rate. Additional time and frequency domain techniques can be applied to further refine the data and improve the accuracy and consistency.

Figure 3:
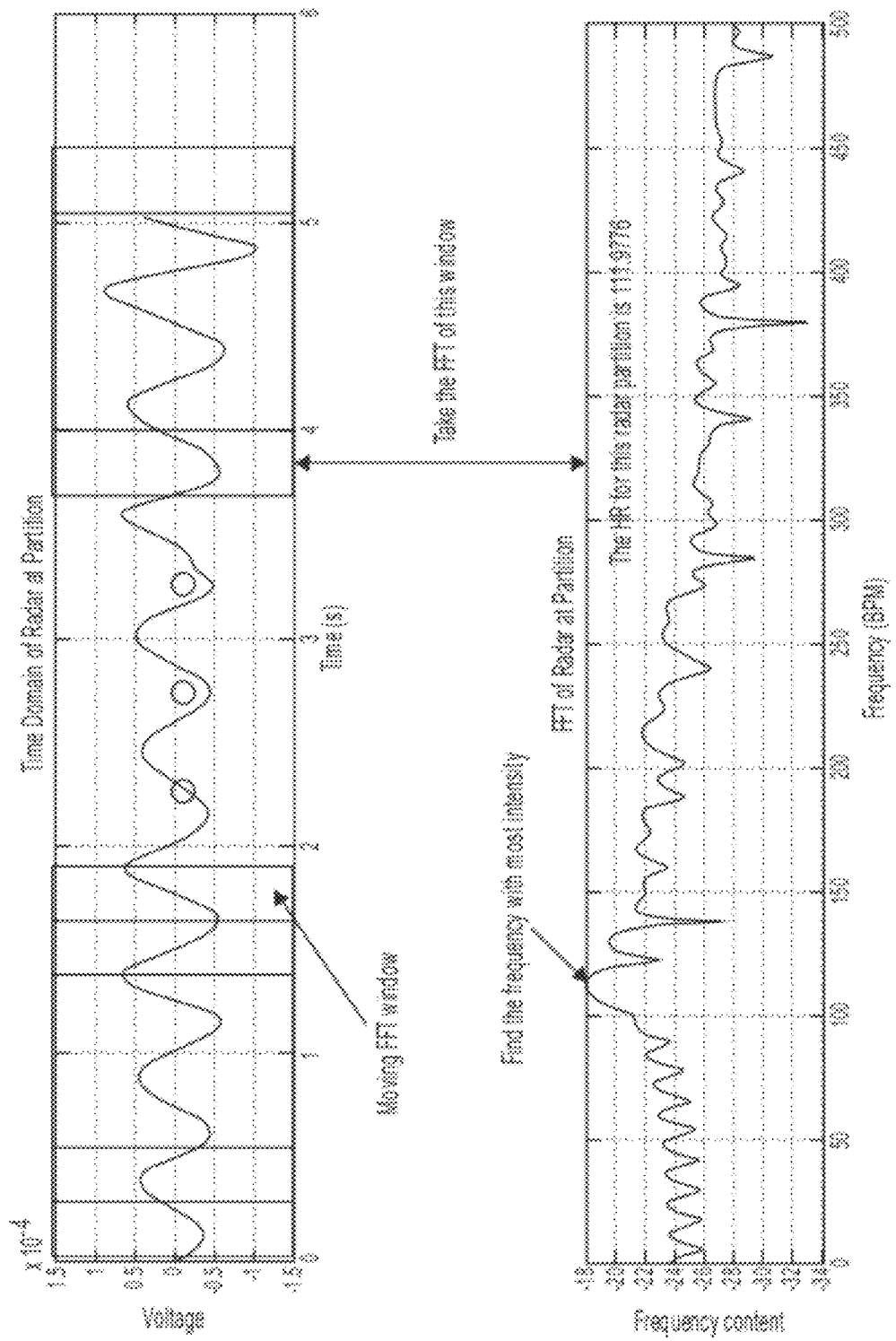
FIG. 3 illustrates a partial analysis of data collected from the system and analyzed using a moving window FFT as described herein.

Referring to FIG. 3, the system may calculate and determine indicators of fetal and/or maternal health in real-time. For example, the system may perform a spectral analysis on ranges of "bins" within the matrix at each various depths of interrogation, as realized by reflections associated with each range bin. A moving Fast Fourier Transform (FFT) window is applied in this example to determine the intensity of every frequency component of the reflected signals over time in each range bin. The frequency with the greatest intensity in each time window may be determined and recorded as a vector in a time plot to provide a visual display of fetal heart rate. The accuracy of this method has been confirmed by comparing measurement of fetal heart rate from with an ultrasonic fetal heart rate monitor.

FIG. 3 illustrates one variations of a process for extracting characteristic indicator of fetal and/or material health invention associated with the spectral analysis. In this example, an indicator (e.g., heart rate) may be determined by calculation using a moving FFT window. The frequency with the greatest intensity in that particular window in this example, is determined be the fetal heart rate.

Figure 4A:
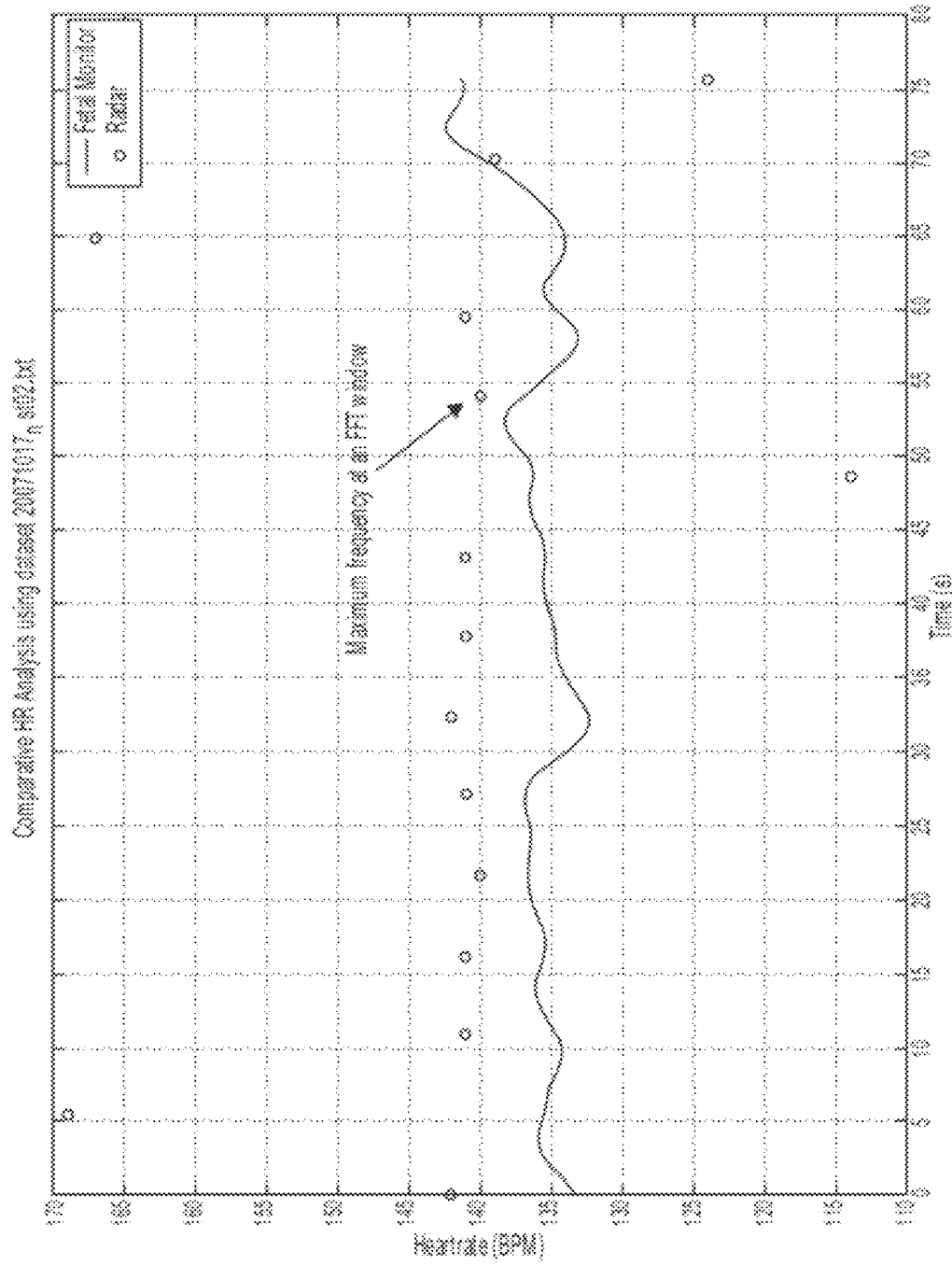
FIG. 4A is a chart showing data taken from a proof-of-concept variation of the system described herein, comparing the system to an ultrasonic fetal monitor in analyzing fetal heart rate.

An early, proof-of-concept model of the system described herein was constructed and used to determine fetal heart rate. One example of some of the data collected from this test device is illustrated in FIG. 4A. FIG. 4A is an illustration of the maximum measured frequency using an early prototype device, compared to an ultrasonic fetal heart rate monitor. In this example, a moving FFT window with a width of 3 seconds was used where 95% of each subsequent window overlaps the preceding window. This application of the moving FFT methodology provides a substantially continuous assessment and measurement of fetal heart rate, minimizing spectral leakage, thereby increasing reliability and confidence in the measured and calculated values. The highly-overlapped moving FFT window process was performed at every range bin to determine if the measured values in each range bin are exhibiting behavior indicative of fetal heart rate.

Figure 4B:
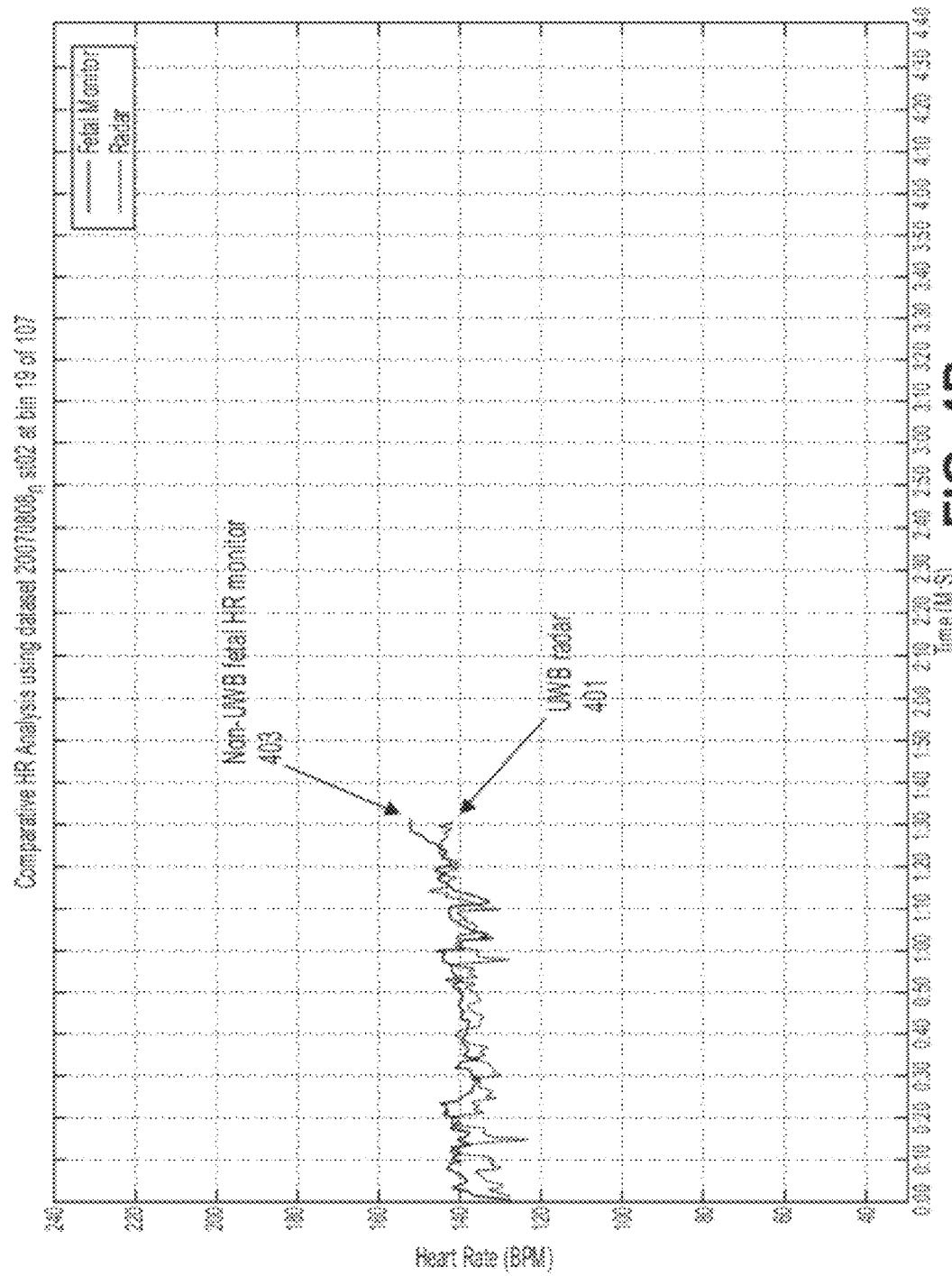
FIG. 4B shows another comparison of a UWB proof-of-concept radar device for measuring fetal heartrate and an ultrasound fetal monitor.

FIG. 4B shows another comparison of the fetal heartbeat determined from the prototype UWB system 401 mentioned above and an off-the-shelf fetal heartbeat monitor 403. The signals compare very closely.

Figure 4C:
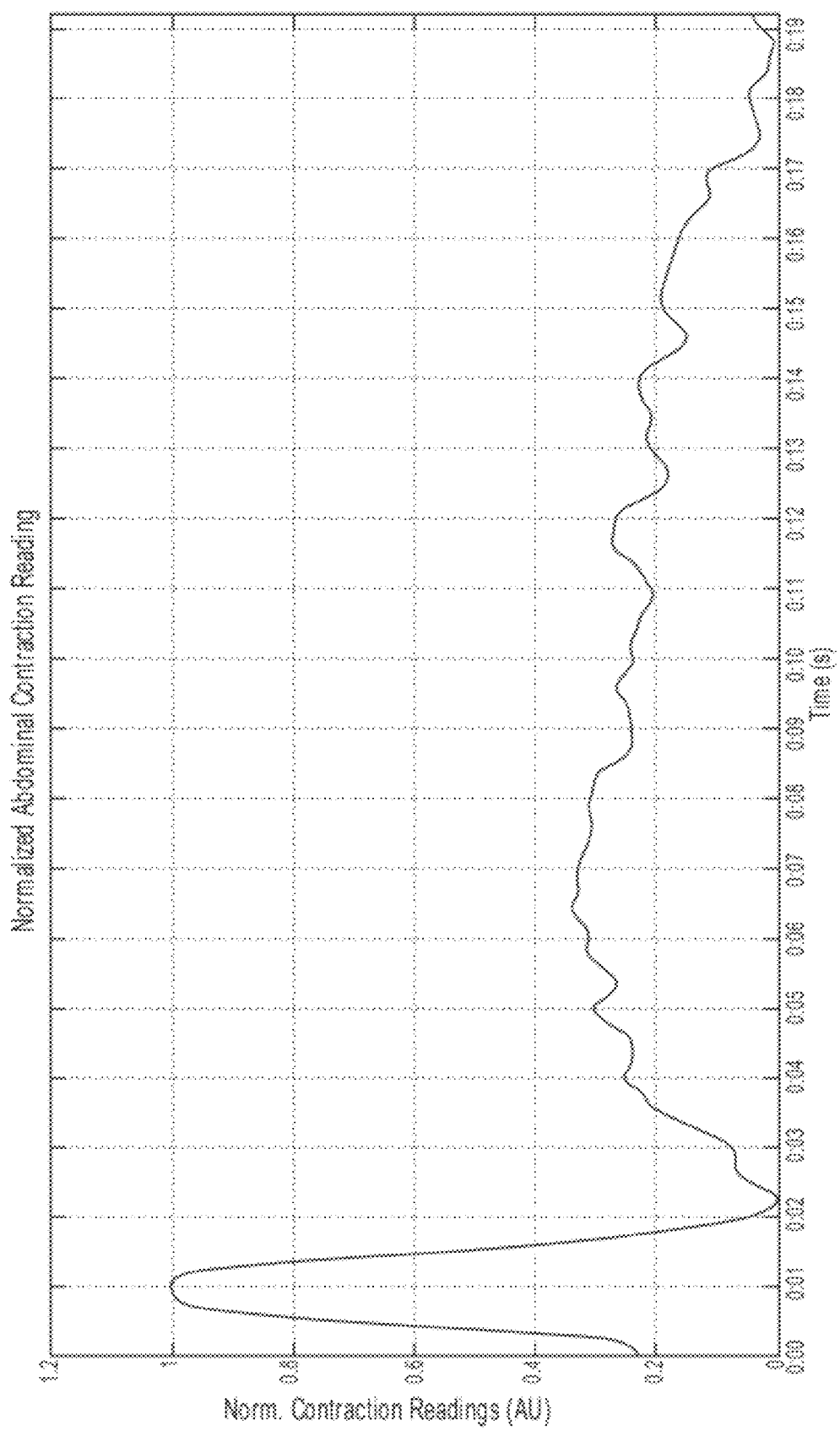
FIGS. 4C and 4D shows the use of the proof-of-concept UWB radar system detecting uterine contractions.
Figure 4D:
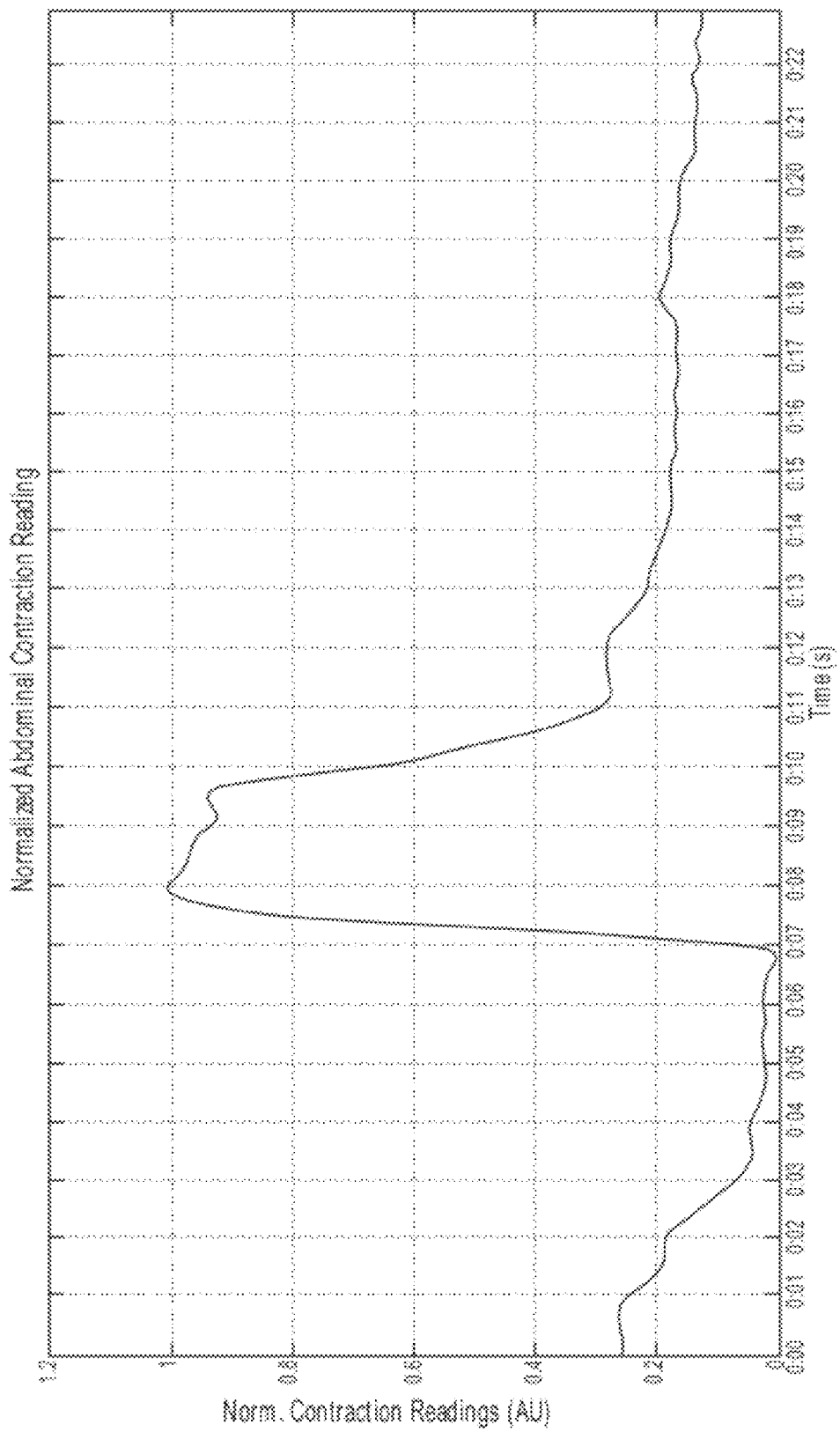

FIGS. 4C and 4D illustrate the extraction of uterine contraction information from the same prototype device. As mentioned above, the same reflection data may be analyzed for simultaneous or parallel determination of the fetal heart beat/rate and maternal uterine contractions. Thus, excessive sampling can be avoided.

A system may examine every range bin for one or more indicators of fetal and/or maternal health in a recurring iterative process; however, every range bin will not necessarily exhibit behavior indicative of one or more indicators. Thus, the system may be tuned to isolate one or more depths to capture reflections from a range bin exhibiting characteristics of the desired indicator(s). In some variations, the system may use landmarks to determine which range of bins to use in determining one or more indicator of fetal and/or maternal health. For example, since the signal may pass completely through the mothers body, markers (e.g., uterine contraction) indicating the region of the mothers body surrounding the fetus may be used to determine the location of the fetus within the depth acquired, and thus the depth may be used to narrow which portions of the matrix to examine when determining the indictors of fetal and/or maternal health. Further, the expended location of physiological markers may help isolate and confirm the indicators examined.

In some variations, the system may include logic to determine whether a transmitted signal has penetrated the mother's tissue sufficiently to reach a known depth of the heart. The penetration metric may be further used by the system to estimate which range bin(s) would most likely exhibit behavior indicative of fetal heart activity. For example, the method may determine the relative permittivity of the tissues to be penetrated by the transmitted signal. Relative permittivity is a unitless constant that is used to calculate the speed of light through different mediums. Table 1, below, shows the values for relative permittivity of various tissues considered in determining whether penetration has been adequate to reach the fetal heart:

TABLE 1

Relative permittivities of tissue types

| TISSUE | RELATIVE PERMITTIVITY |
|---|---|
| Dry skin | 36.59 |
| Muscle | 50.82 |
| Fat | 5.12 |
| Uterus | 55.31 |
| Amniotic Fluid | 60.00 |

The known permittivities are incorporated in the radar distance equation, described below in Equation 1.

$$d = \frac{v}{2f} = \frac{c}{2\sqrt{\varepsilon_r}\,f} = \frac{ct}{2\sqrt{\varepsilon_r}} \quad \text{(Equation 1)}$$

With different permittivities at different depths in different range bins, as shown in Equation 2 below, the relationship is then expanded to:

$$\sum_{i=1}^{W} t_i = \sum_{i=1}^{W} \frac{2d_i\sqrt{\varepsilon_r}}{c} = \frac{2}{c}\sum_{i=1}^{W} d_i\sqrt{\varepsilon_{r_i}} \quad \text{(Equation 2)}$$

With this relationship determined, the system may determine the travel time required for the transmitted signals to reach the fetal heart (or other fetal/maternal anatomical marker) for a particular subject. In one version, where the system uses a fixed return time. This return time may be used to determine when or if the transmitted signal reaches the heart of the fetus (or other marker). For example, as shown by Equation 3, below, in one circumstance, we can determine that the return time for the last range bin is 5.7 nanoseconds (ns). This value may be dependent on presumptions or estimates of the thickness of the encountered tissue segments. Typically, the thickness of skin, fat and distance to the fetal heart may be known.

$$\Sigma_{i=1}^{W} t_i \leq 5.7 \text{ ns} \quad \text{(Equation 3)}$$

In calibrating a system using a fixed return time, it may be useful to presume that the relative permittivity of other tissues or mediums encountered by the transmitted signal, excluding skin and fat, are equal. For example, in one version, the overall relative permittivity is assumed to be the mean of the relative permittivity of the uterus, amniotic fluid, and muscle, resulting in a value of 55.38. In this circumstance, where the transmission parameters are fixed, it is possible to determine if the sensor is capable of interrogating the heart of the fetus for each individual mother. In certain cases, the mother's physiologic configuration and structure may not allow using a particular fixed calibration to image the fetal heart.

The location of moving anatomical features (e.g., fetal heart, fetal body, the mothers heart, uterus, etc.), the reflected signals may present moving images of what is present in the different "bins" of the matrix. Thus, the change in the energies reflected in each bin may be used to determine the various frequencies of movement, and therefore the various indicators examined. The system may analyze a range of bins.

Figure 5:
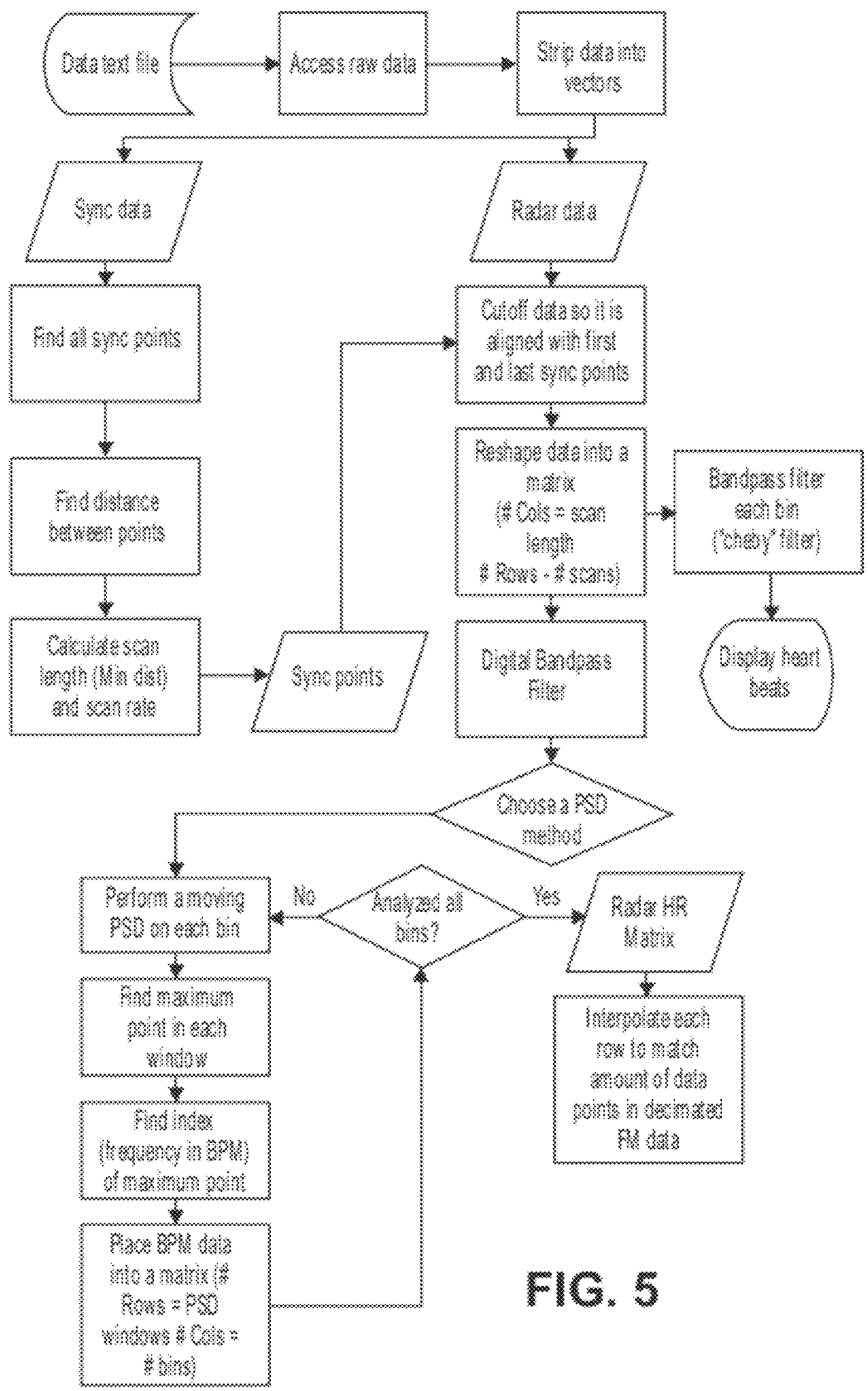
FIG. 5 illustrates one variation of a method for determining an indicator of fetal health (e.g., fetal heart rate) from the matrix of reflected values, as described herein.

FIG. 5 illustrates one method of determining an indicator of fetal health (e.g., fetal heart rate) using the system described herein.

Fetal heart rate may be determined by detecting peaks in the fetal heart beat signal and calculating the period between consecutive heart beats, and inverting the period to calculate the rate. Specifically, one method of detecting heart beats within the data may be done in multiple steps. A finite segment of the waveform may be acquired and a bandpass filter can be applied to emphasize the fetal heart rate waveform. An auto-correlation function may be used to emphasize any periodic motion observed within the data segment. The periodic motion expected to be observed may correspond to the fetal heart beat. An algorithm may then be used to find local maximums of a data segment, corresponding to the peak of a single heart beat waveform. The number of samples between consecutive peaks can be calculated, and based of the sampling rate, the period of fetal heart beats can be calculated. The fetal heart rate may be calculated by taking the inverse of the fetal heart period.

Similarly, the devices described herein may be used to determine uterine contractions from one or more location corresponding to the uterine wall. In one variation, the maternal contractions may be detected by calculating large differences in the offset of the radar return at various times. A state of equilibrium may be determined by computing the mean of the radar return signal over a several seconds. A contraction can then be detected by calculating the standard deviation between the offset in an equilibrium state to the offset level during the contraction. If the standard deviation is larger than a given threshold, it can be assumed that the large change in standard deviation was caused by a maternal contraction. The threshold may be determined through several tests of maternal contractions In operation, the systems and methods described herein support the monitoring and assessment of a plurality of features which can provide useful information concerning both fetal and maternal health during pregnancy, and, delivery. For example, the system may monitor the movement associated with a fetus within a mother's womb (body movement) as well as other features such as maternal contraction rate and/or strength, or the like. The plurality of indicators of fetal and/or material health monitored may be used to generate a combined maternal/fetal index (NMI) based upon measurements of various functions relative to the health of the fetus. Much as it is important to establish an adult cardiac or respiratory NMI to allow assessment of departure from the relevant NMI, the system described herein correspondingly supports noninvasive collection of critical data from the fetus, including overall body movement, heart rate and rhythm, associated variability and periodic respiration, which may be used to create an overall fetal NMI. Following are descriptions of components of a fetal NMI which may be used. Of course, the individual indicators may also be presented or applied individually, and may be converted to a familiar form (e.g., beats/min for heart rate, etc.) or left unconverted.

For example, the system may allow non-invasive automated tracking of fetal movement in the mother's womb, oftentimes referred to as "kick counting", which supports a much more accurate and clinically meaningful way to assess fetal health over manual kick counting techniques. Separately, the present invention also supports monitoring new born body movement and respiration. Each of these parameters can be monitored and assessed by the system.

In some variations, the system monitors a plurality of physiological movements simultaneously, to develop a number of individual NMI's which are then integrated to create an "Aggregate NMI" indicating a desired state for the subject with reference to a particular area of observation. For example, only one sensor may be required to collect the desired data, providing multiple indicators simultaneously. In some versions, data from two or more UWB sensors or an array of sensors may be used to increase data availability and accuracy. For example, one version of an aggregate NMI is a cardiopulmonary NMI where the cardiac and respiratory NMI's are aggregated to develop a measure which might indicate when a subject (fetus and/or mother) is departing from a desired NMI toward an abnormal condition, such as bradycardia or tachycardia. As long as normal motion occurs, a physician will be less likely to be concerned with the overall health of a patient. However, deviation from a selected NMI, suggesting "abnormal" motion or activity, may be signaled to a physician able to preemptively respond to the causes of the departure from the NMI. Thus, the system can monitor and track abnormal physiological motion to allow early, pre-emptive response by a physician or medical caregiver.

For example, the system may allow determination of fetal, maternal and newborn health by monitoring multiple indicators (preferably simultaneously or using the same matrix), and may use the indicators to generate one or more NMI's, allowing subsequent monitoring for departure from a predicted or expected NMI range. Any departure from expected (predetermined) NMI or individual indicator(s) may be registered by the system and may provide early notice to the treating physician, and, the mother, of a need to obtain medical care to avoid any complications associated with the health of the fetus, the newborn, or the mother herself. The system is particularly well-suited to determining FHR variability on a beat-to-beat basis, and, long-term trend analysis.

The system may also detect and monitor fetal movement in the mother's womb, as mentioned above. Reduction of movement is a clinically recognized reliable measure of fetal distress in the last trimester of pregnancy and can be combined with measurements of FHR, FHR variability and fetal respiration. Current methods of assessing fetal distress rely primarily on either ultrasound, direct maternal observation of fetal movement or an extremely intrusive fetal EKG, typically requiring application of a fetal scalp monitor while the fetus is still in the mother's womb. These methods are either prone to errors in observation (inaccurate counts by the mother), require specialized equipment unsuitable for home use (ultrasound), or provide false positives such as artifacts of recording (EKG). The systems described herein may deliver a unique, portable and reliable device that does not require bulky equipment, a technician to operate the system, or, the use of unreliable elements such as electrodes. Combined with the ability to establish a personalized NMI for each pregnancy, the system may provide a method to provide early indications of potential pregnancy problems through identification of a departure from expected values of individual indicators or NMI's to avoid later catastrophic events, such as premature birth or meconium aspiration.

Concurrent with direct observation of fetal movement and comparison to a fetal movement NMI, the system may also be used to simultaneously track departure from a maternal NMI, as mentioned. For example, the system can track changes in mother's cardiac function which is an indicator of preeclampsia, a common condition during pregnancy. Additionally, the system may allow a subject-specific NMI to be developed to track expected significant increases in stroke volume and cardiac output in the second and third trimesters of pregnancy, thereby avoiding the suggestion of problems where Sudden Infant Death Syndrome (SIDS) is of great concern to parents of newborns and has resulted in the development and marketing of a variety of baby monitoring devices intended to avoid SIDS. SIDS and other abnormalities of respiration or cardiac function in newborns and older babies can be reliably monitored by the system at home thus adding a dimension of protection through detecting cardiac arrest or arrhythmias or respiratory failure in babies. Additionally, the use of the NMI and departure from the NMI is essential when providing feedback to a lay user, such as a mother or father of the newborn.

For example, the devices and systems described herein may be adapted for use with a newborn or infant and configured for monitoring the infant or newborn to prevent SIDS. In some variations, a system for monitoring a newborn or young infant may include a sensor (e.g., a disposable sensor or a reusable sensor) and a processor (either local or remote) for receiving reflection (UWB) data from the sensor. One or more sensors may be used as part of the SIDS monitor, in any of the configurations described herein.

In any of the systems and devices described herein, the system may include a UWB generator or source. The UWB generator typically generates the UWB pulse or pulses, and may configured the pulse as desired, both in timing and composition. Any of the components described herein may be connected to a power source, which may be battery, rechargeable, or a wall or other external power adapter. In many of the variations described herein the system includes a timer or synchronizing timer as mentioned. For example, a synchronizing timer may coordinate the application of the UWB pulse with the signal processor to aid in forming the matrix as described herein.

Any of the variations described herein may include a controller (e.g., system controller) which may be a separate element or be integral to one or other components, including the signal processor. The controller may include control logic for triggering UWB signal emission and timing of the overall system. In some variations the controller includes one or more user inputs for activating the system/device, for de-activating the system/device, or for modifying the behavior of the systems/device. Inputs may be buttons, dials, sliders, touch screens, or receivers for receiving remotely provided instructions. Instructions provided to the controller may allow modification of the parameters (e.g., the indicators of health) being monitored, or they may modify the timing (when the system is configured to automatically turn on/off or pulse).

These systems, devices and methods may be used to track fetal heart rate (FHR) variability, a key indicator of fetal distress. The FHR is under constant variation from a baseline. This variability reflects a healthy nervous system, chemoreceptors, baroreceptors and cardiac responsiveness. Prematurity decreases variability; therefore, there is little rate fluctuation before 28 weeks. Variability should be normal after 32 weeks. Fetal hypoxia, congenital heart anomalies and fetal tachycardia also cause decreased variability. Beat-to-beat or short-term variability is the oscillation of the FHR around the baseline in amplitude of 5 to 10-beats per minute (BPM). Long-term variability is a somewhat slower oscillation in heart rate and has a frequency of three to 10 cycles per minute and amplitude of 10 to 25 BPM. Clinically, loss of beat-to-beat variability is more significant than loss of long-term variability and may be ominous. The system is capable of tracking this loss of beat-to-beat variability by virtue of several novel aspects and the synergistic combination of these novel aspects. First, the system may be less reliant on optimal sensor positioning since it interrogates a large volume including the FHR activity. Second, the system tracks and measures actual cardiac tissue movement rather than electrical signals indicative of cardiac activity. Third, the system is not dependent on maintaining an electrical or acoustic contact with the subject, and can compensate for changes in position of the fetus. Fourth, the system can be used in a noninvasive manner at any time without prior application of electrodes or an acoustic gel. Fifth, the system uses a plurality of interrogation depths to ensure the acquisition of data indicative of fetal cardiac activity. Sixth, the system may quickly and accurately separate out maternal heart rate which will generate an erroneous reading of FHR variability. Seventh, the system includes a plurality of methods which are used to cross-check the FHR activity. Eighth, the system collects data from the target interrogation volume at a very high frequency and with high resolution and fine granularity, allowing a more detail assessment of FHR variability to be performed on a beat-to-beat basis and in real-time. Ninth, the system avoids the need to use extremely invasive components such as a fetal scalp electrode, avoiding the potential of causing more harm from the monitoring. Tenth, the system supports the introduction of new analyses which may provide additional information concerning fetal distress.

As mentioned above, one or a plurality of UWB sensors may be used with the devices and systems described herein. For example, the systems may include a plurality of UWB sensors. Each sensor may include one antenna configured as both the Tx and Rx antenna, or the sensor may include a plurality of antenna, such as a separate Tx and Rx antenna. If a single antenna for both Tx and Rx is used, the antenna may include an RF switch between the transmitter, receiver, and antenna elements.

When more than one antenna is used (e.g., including more than one sensor), the system may have a predetermined or settable coupling or assignment between the sets of antennas. For example, multiple pairs of antennas are used and may be coupled so that each Rx antenna (or Rx capable antenna) is coordinated with a specific Tx antenna, which does not necessary have to be the same as the Tx antenna on the individual sensor. For example, multiple UWB sensors may be used at different positions on the mother, where each sensor includes a pair of Tx and an Rx antenna. These sensors and their Rx and Tx antenna could configured to operate in one of two basic modes, such as monostatic or multistatic (e.g., bistatic). Monostatic radar operates so that the Tx and Rx antennas are co-located (as in traditional UWB radar) while multistatic systems allow the Tx antenna and one or more Rx antennas that are not co-located to operate together. For example, the Tx/Rx pair on a sensor positioned at the top of the mother's abdomen could transmit the pulse while one or more receive antennas located in a second location (e.g., at the bottom of the abdomen) could receive the reflections from the transmitted pulses. Multistatic techniques could be used to improve the quality of the reflected signal. For example, multi-static operation may improve the signal if a major surface of the fetal heart is not close to perpendicular to the direction of propagation (best reflections). Thus, in some variations the system may include one or more "master" sensor with a Tx antenna and one or more "slave" sensors with relieving (Rx) antenna. The system may also generalize the bistatic (2 antenna) case to a true multistatic (two or more receive antennas) case, which could also support forward scatter techniques. In forward scatter, one sensor including a Tx/Rx antenna pair is positioned in a first location (e.g., on the left side of the mother's abdomen) and a second sensor including a pair of Tx/Rx antenna is positioned on a second location, such as on the right side of her abdomen. Thus, the left Tx signal may be received by the right RX antenna and visa versa. These techniques can be used to better isolate and track fetal activity.

The system described herein may also be adaptive. For example, one or more system parameters may be modified to optimize the desired received reflections while simultaneously minimizing undesired received reflections. For example the system may automatically and/or manually allow switching from monostatic to bistatic operation. In some variations, the system may collect maternal heart and/or respiration data and filter or subtract this from the suspected fetal data. In some variations, the system is configured to correlate received reflections with stored models of fetal and/or maternal health indictors such as fetal heart motion to better isolate the indicators.

In operation, the fetal monitors described herein may be used during virtually any stage of the labor and delivery process, unlike currently available monitors, which are limited based on the location and activity of the fetus within the mother. Thus, the systems and devices described herein may be used to allow continuous monitoring of the fetus as the mother transitions from labor to delivery, or even the OR for a C-section. For example, a multi-antenna (multi-sensor) system may be used in which one or more sensors having Tx/Rx antennas could be repositioned dynamically (flex arms or wireless transceiver modules) to minimize interference with delivery or surgical preparation.

As mentioned, above, the sensors (including Rx and Tx antenna, as well as pre-processing electronics and/or logic) may be disposable. For example, a disposable sensor with antenna could be configured for skin contact with the mother, e.g., adhesively. For sanitary purposes, the sensor element with antenna could be disposed after each use. The antenna assemblies may include the RF signal amplifiers for pre-processing, as mentioned.

In some variations, the system is adaptable to reduce or limit the energy applied to that which is necessary for a clear signal, while minimizing the total energy exposure to the mother and/or fetus. For example, a system capable of adaptively adjusting the transmitted energy level may include an automatic measurement of RF energy level of the received indicator, such as the fetal heart beat. The system may then perform a comparison of measured energy level with a target energy level. The difference can then be provided to the transmitter for either increasing or decreasing the transmitted energy level so that the received energy level meets the desired target level. This compensation permits the fetus to have no greater exposure to RF than necessary yet compensates for variation in pregnant mothers anatomy.

Any of the devices or systems described herein may also be part of a system including a server, network, or other elements that allow access to the measured and/or calculated data either in real-time or from recorded information. For example, in some variations, the systems described herein include a UWB sensor having a Tx/Rx antenna (or pair of antenna) with a processor for signal processing and system management; the system may also include local memory. Data that is captured in one or more test sessions may be stored in the local sensor memory. Test data may be transferred either wirelessly or wired to a computer system or monitoring system, which may include a server. For example test data may be transferred wirelessly to a wireless network modem and in turn transferred to a networked server. The data may be stored on the server for retrieval by a computer system, handheld smartphone, or medical instrumentation. The retrieved information can then be displayed, analyzed, or printed by the computer system, smartphone, or medical instrumentation. In this example, the server, network or monitoring system may be considered part of the system, or separate from it.

In some variations, the wireless network and associated server is capable of simultaneously transferring data from multiple sensors to the networked server.

Figure 6:
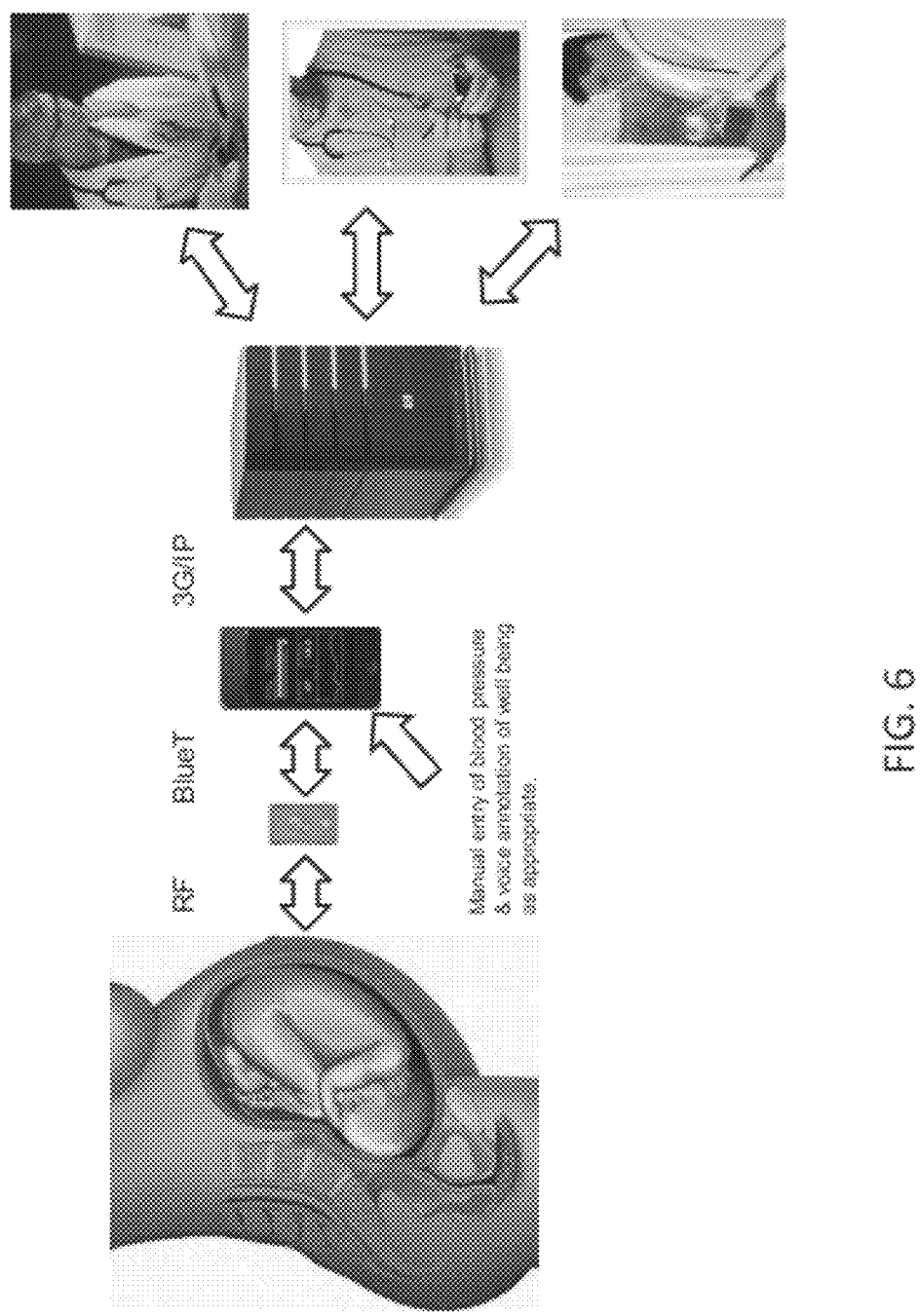
FIG. 6 illustrates one variation of UWB fetal monitoring system as described herein.

FIG. 6 illustrates one variation of a system including a server for passing along information regarding two or more indicators of fetal or fetal and maternal health. In this example, the system includes a UWB sensor having a pair of antenna. The miniature sensor in this example consists of one or more UWB radar transceivers, an embedded processor, local non-volatile memory, a user interface, a rechargeable battery, and a wireless communications link—e.g. Bluetooth. The UWB radar transceiver(s) will generate a series of the UWB impulses and receive the resultant reflections based on round trip time of flight from the UWB transceiver to the anatomical depth of interest. The transceiver(s) can be co-located in the case housing the balance of the sensor circuitry or housed in a separate detachable case that connects with the sensor base. A detachable case for the transceiver would allow for removal and replacement of the portion of the sensor that makes contact with the patient. Connection between the detachable case and the sensor base would consist of an electrical connector and a mechanical fastener.

The embedded processor in this example is responsible for overall control of the sensor, collection and pre-processing of the radar data, identification of fetal and uterine activity, local storage of the data, interaction with the mother, and transfer of the data to the smart phone. Radar parameters under programmatic control will include the state of the radar (enabled/disabled), the pulse repetition frequency (PRF), the focal depth, transmitted power, receiver gain, and the scan rate.

The received radar data will be digitized and processed by the embedded processor. Basic processing may include noise reduction and isolation of anatomical motion. Once isolated, objects in motion may be further analyzed using a variety of techniques to determine whether the motion corresponds to fetal heart activity, fetal motion, or uterine contractions. Fetal heart activity may be isolated using a combination of time and frequency domain techniques in conjunction with pattern recognition. Measurement of the cardiac intra-beat interval may utilize high-pass filtering of the cardiac returns to reduce the time spread of the cardiac reflections, providing a more discrete waveform to increase measurement accuracy. Motion data corresponding to suspected uterine contractions will be correlated with results obtained using static techniques based on relative range from the radar to the various anatomical layers, such as fat, uterus, and amniotic sack; and the fetus. Processed data consisting of fetal cardiac activity, fetal motion, and uterine contractions may be stored locally in non-volatile memory along with timestamps. The sensor may contain sufficient memory to store data from multiple test procedures.

The embedded processor may interact with the mother through a combination of audible and visual indicators as well as one or more switches. The audible indicator, if included, may consist of an audio speaker and associated drive circuitry. The processor may then synthesize an audible tone, such as one mimicking the traditional cardiac "lub-dub" pattern familiar from auscultation. The audio pattern may be proportional to the fetal heart rate and radar signal amplitude, allowing the user (including a mother) to optimize the position of the sensor by maximizing the audio tone. The visual indicators may, at a minimum, consist of a power on light and a light to indicate data collection is in progress. Additional visual indicators could include a light source that blinks at the fetal heart rate or a numeric display—e.g. an LCD panel that indicates the fetal heart rate. The level of the battery charge could be communicated to the mother through modulation of the power on light or if included, an icon on the numeric display. Completion of the test could be signaled through both the audible and visual indicators. Manual switches will at a minimum include a power control, a volume control, and a mute button. The sensor will have an auto-shutoff feature that will automatically disable the radar if the sensor is not on the body, or if it has been in use well beyond its recommended usage.

In the example shown in FIG. 6, when the sensor is placed in the cradle and queried by the smart phone, the processor may retrieve the data from memory and upload the data to the smart phone. Data integrity can be assured through standard wireless transfer methods including checksums and transfer acknowledgement protocols. As mentioned above, the sensor may include other transducers to improve the accuracy and physiological signal isolation. These transducers could include an accelerometer or pressure transducer.

The example shown in FIG. 6 also includes a charging cradle. A charging cradle may be responsible for charging the battery in the sensor. It may also be used to hold the sensor when not in use. Finally the cradle may enable the wireless communications circuit in the sensor, preventing transmission of data when the sensor is on the mother, further reducing RF exposure to the mother and fetus.

The system shown in FIG. 6 also includes a communication device. A communication device may be included or incorporated to provide several capabilities. For example, a communication device such as a "smartphone" that may run an application specific for the fetal monitor sensor. Comparable capabilities may be enabled for a range of commercially available smartphones and PDA's.

For example, in FIG. 6, the system may operate in a first mode that is a scan mode to help the user configure the place of the sensor. The system may also include a second mode to display the summary data and to send the summary data to the health care provider through their server. As mentioned above, the communication device may provide feedback to the user when the sensor is in scan mode. The smartphone or PDA may activate the speaker system and notify the user if the sensor is in place or not. Once the application has notified that the sensor is in place, the PDA/smartphone may then update the fetal/maternal health indicator, e.g., fetal heart rate, at every minute or other appropriate interval. This mode can be used as a tool for placement at the user's discretion, and is not required in the testing process. However, the application may be used to acquire all summary data from the sensor and send the data to the health care provider.

In this example, the complete data transfer process may be initiated when the scan is complete and the application initiates communication. The communication device may be able to access the sensor for all of the data with the smartphone application. Once the application is open, the application will communicate with the sensor to see if the data in flash memory is current. If the data is current the user can execute the transfer of data to be analyzed, otherwise the transfer will not occur. Once the data is analyzed a graphic of the summary data will appear in the application screen. The summary will show graphs, or other summary, of one or preferably more of the indicators of fetal/maternal health. For example, the summary may show a graph of the fetus' heart rate, markers of the occurrences of fetal movement and also markers of the occurrences of contraction, all against time.

When the user is ready to send the data to the health care provider, the application may allow the user to send the summary data, e.g., with a push of a button. The smartphone application may act as an email provider in that it will save the data into a tab delimited text file and attach it to an email. The summary data may be automatically saved to the smartphone/PDA's memory and at any time, the user can view the summary data. The application may also give the user a comprehensive summary over 2 or more tests to monitor the fetus' condition or a week's period or more.

What is claimed is:

1. An ultra-wideband (UWB) fetal monitoring system capable of concurrent monitoring of indicators of fetal and maternal health, the system comprising:
   a sensor configured to transmit a UWB signal and receive reflected UWB signal data, the sensor comprising at least one antenna; and
   a signal processor configured to receive the reflected UWB signal data from the sensor, wherein the signal processor is programmed to:
   process the reflected UWB signal data into a matrix of reflected UWB signals indexed by depth and time,
   identify which reflected UWB signals in the matrix of reflected UWB signals correspond to a uterine contraction,
   differentiate between fetal and maternal regions within the matrix of reflected UWB signals based on the identification of which reflected UWB signals correspond to the uterine contraction,
   extract one or more indicators of fetal health from the fetal region within the matrix of reflected UWB signals, and
   extract one or more indicators of maternal health from the maternal region within the matrix of reflected UWB signals; and
   a transmitted energy level adapter configured to adjust the energy level of the UWB signal transmitted by the sensor based on the energy level of the signals reflected by the fetus,
   wherein the transmitted energy level adapter comprises a comparator configured to compare the energy level of signals reflected by the fetus to a predetermined target energy level, further wherein the transmitted energy level adapter is configured to adjust the energy level of the UWB signal to keep the energy level of signals reflected by the fetus within the predetermined target energy level.

2. The system of claim 1, wherein the sensor comprises a receiving antenna and a transmission antenna.

3. The system of claim 1, wherein the sensor comprises a combined antenna configured for receiving and for transmission.

4. The system of claim 1, further comprising a plurality of sensors each configured for receiving and transmission of UWB data and comprising at least one antenna.

5. The system of claim 4 configured for monostatic operation, wherein the transmission of the UWB signal from each sensor is received by the same sensor.

6. The system of claim 4 configured for multistatic operation, wherein the transmission of the UWB signal from one sensor is received by a different sensor.

7. The system of claim 1, wherein the signal processor is configured to determine one or more indicators of fetal health selected from the group consisting of: fetal heart rate, fetal heart rate variability, fetal respiration, fetal body movement.

8. The system of claim 1, wherein the signal processor is configured to determine one or more indicators of maternal health selected from the group consisting of: maternal heart rate, maternal contraction rate, maternal blood pressure, maternal respiration.

9. The system of claim 1, further comprising a receiver connected to the antenna, the receiver configured to receive reflections of emitted signals received by the antenna and process them into data to be passed on to the signal processor.

10. The system of claim 9, wherein the receiver is configured to amplify signals based on their depth so that signals reflected further from the sensor are amplified more than signals reflected closer to the sensor.

11. The system of claim 1, wherein the signal processor is configured to determine fetal heart rate from the fetal region within the matrix of reflected UWB signals and uterine contraction rate from the maternal region within the matrix of reflected UWB signals.

12. The system of claim 1, further comprising a local memory for storing the matrix information.

13. The system of claim 1, further comprising a communication circuit for communicating to a monitoring system.

14. The system of claim 13, wherein the monitoring system comprises a computer system configured to store and transmit data.

15. The system of claim 13, wherein the monitoring system comprises a networked server.

16. The system of claim 1, wherein the sensor is configured as a single-use, disposable sensor configured to couple and uncouple from the signal processor.

17. The system of claim 1, further comprising a non-UWB sensor.

18. The system of claim 17, wherein the non-UWB sensor comprises an accelerometer.

19. The system of claim 1, further comprising an output configured to present the one or more extracted indicators of fetal or fetal and maternal health.

20. The system of claim 19, wherein the output is configured to present at least one of the extracted indictors as a chart recording.

21. An ultra-wideband (UWB) fetal monitoring system capable of concurrent monitoring of indicators of fetal and maternal health, the system comprising:
  a sensor configured to transmit a UWB signal and receive reflected UWB data, the sensor comprising at least one antenna;
  a transmitter connected to the antenna, the transmitter configured to generate a series of low voltage, short-duration broadband pulses for transmission as an emitted signal from the antenna as an ultra-wide band spectrum signal; and
  a signal processor configured to receive the reflected UWB data from the sensor, wherein the signal processor is programmed to:
  process the reflected UWB signal data into a matrix of reflected UWB signals indexed by depth and time,
  identify which reflected UWB signals in the matrix of reflected UWB signals correspond to a uterine contraction,
  differentiate between fetal and maternal regions within the matrix of reflected UWB signals based on the identification of which reflected UWB signals correspond to the uterine contraction,
  extract one or more indicators of fetal health from the fetal region within the matrix of reflected UWB signals, and
  extract one or more indicators of maternal health from the maternal region within the matrix of reflected UWB signals; and
  a transmitted energy level adapter configured to adjust the energy level of the UWB signal transmitted by the sensor based on the energy level of the signals reflected by the fetus,
  wherein the transmitted energy level adapter comprises a comparator configured to compare the energy level of signals reflected by the fetus to a predetermined target energy level, further wherein the transmitted energy level adapter is configured to adjust the energy level of the UWB signal to keep the energy level of signals reflected by the fetus within the predetermined target energy level.

22. An ultra-wideband (UWB) fetal monitoring system for monitoring indicators of fetal and maternal health, the system comprising:
  a sensor configured to transmit a UWB signal and receive reflected UWB data, the sensor comprising at least one antenna, a power source and a transmitter configured to generate a series of low voltage, short-duration broadband pulses for transmission as an emitted signal from the antenna as an ultra-wide band spectrum signal; and
  a communications device configured to receive information from the sensor and to pass the information on to a signal processor, wherein the signal processor is programmed to:
  process the reflected UWB signal data into a matrix of reflected UWB signals indexed by depth and time,
  identify which reflected UWB signals in the matrix of reflected UWB signals correspond to a uterine contraction,
  differentiate between fetal and maternal regions within the matrix of reflected UWB signals based on the identification of which reflected UWB signals correspond to the uterine contraction,
  extract one or more indicators of fetal health from the fetal region within the matrix of reflected UWB signals, and
  extract one or more indicators of maternal health from the maternal region within the matrix of reflected UWB signals; and
  a transmitted energy level adapter configured to adjust the energy level of the UWB signal transmitted by the sensor based on the energy level of the signals reflected by the fetus,
  wherein the transmitted energy level adapter comprises a comparator configured to compare the energy level of signals reflected by the fetus to a predetermined target energy level, further wherein the transmitted energy level adapter is configured to adjust the energy level of the UWB signal to keep the energy level of signals reflected by the fetus within the predetermined target energy level.

23. The system of claim 22 wherein the signal processor is configured to determine fetal heart rate and maternal contraction rate from the matrix.

24. The system of claim 22, further comprising an output configured to display one or more of the plurality of indicators of fetal or maternal health.

25. The system of claim 22, further comprising a charging cradle configured to charge the power source.

26. The system of claim 1, wherein the signal processor is further programmed to apply a peak detection algorithm on the matrix of reflected UWB signals to identify which reflected UWB signals correspond to a uterine contraction.

* * * * *